US012692471B2

(12) United States Patent
Sevenler et al.

(10) Patent No.: US 12,692,471 B2
(45) Date of Patent: Jul. 28, 2026

(54) HIGH ASPECT RATIO DEVICES AND METHODS FOR VITRIFICATION OF BIOLOGICAL SAMPLES BY RAPID COOLING

(71) Applicants:The General Hospital Corporation, Boston, MA (US); TRUSTEES OF TUFTS COLLEGE, Boston, MA (US)

(72) Inventors: Derin Sevenler, Charlestown, MA (US); Rebecca Sandlin, Melrose, MA (US); Mehmet Toner, Charlestown, MA (US); Giovanni Widmer, Newton, MA (US); Saul Tzipori, Shrewsbury, MA (US); Justyna Jaskiewicz, Boston, MA (US)

(73) Assignees: The General Hospital Corporation, Boston, MA (US); Trustees Of Tufts College, Medford, MA (US)

( * ) Notice: Subject to any disclaimer, the term of this patent is extended or adjusted under 35 U.S.C. 154(b) by 716 days.

(21) Appl. No.: 17/912,938

(22) PCT Filed: Mar. 19, 2021

(86) PCT No.: PCT/US2021/023329
§ 371 (c)(1),
(2) Date: Sep. 20, 2022

(87) PCT Pub. No.: WO2021/189001
PCT Pub. Date: Sep. 23, 2021

(65) Prior Publication Data
US 2023/0365914 A1 Nov. 16, 2023

Related U.S. Application Data

(60) Provisional application No. 62/992,413, filed on Mar. 20, 2020.

(51) Int. Cl.
*C12N 1/04* (2006.01)
(52) U.S. Cl.
CPC ...................................... *C12N 1/04* (2013.01)
(58) Field of Classification Search
CPC ...................................................... C12N 1/04
See application file for complete search history.

(56) References Cited

U.S. PATENT DOCUMENTS

| | | | |
|---|---|---|---|
| 6,065,294 A | 5/2000 | Hammerstedt et al. | |
| 2009/0305224 A1 | 12/2009 | He et al. | |
| 2018/0094232 A1 | 4/2018 | Toner et al. | |
| 2019/0162639 A1* | 5/2019 | Gutelius ................. | G01K 13/12 |
| 2019/0200603 A1 | 7/2019 | Mohanty et al. | |
| 2021/0244019 A1* | 8/2021 | Schyver ................. | B65B 3/003 |

FOREIGN PATENT DOCUMENTS

| | | |
|---|---|---|
| WO | WO 1996/024018 | 8/1996 |
| WO | WO 2018/232110 | 12/2018 |
| WO | WO 2019/204821 | 10/2019 |

OTHER PUBLICATIONS

Jaskiewicz, Justyna J., et al. "Cryopreservation of infectious Cryptosporidium parvum oocysts." Nature communications 9.1 (2018): 2883. (Year: 2018).*
Akiyoshi et al., "Characterization of Cryptosporidium meleagridis of Human Origin Passaged through Different Host Species," Infect Immun., Apr. 2003, 71(4):1828-1832.
Black et al., "Comparison of assays for Cryptosporidium parvum oocysts viability after chemical disinfection," FEMS Microbial. Lett., Jan. 1996, 135(2-3):187-189.
Checkley et al., "Effects of Cryptosporidium parvum infection in Peruvian children: growth faltering and subsequent catch-up growth," Am. J Epidemiol., Sep. 1998, 148(5):497-506.
GBD 2016 Disease and Injury Incidence and Prevalence Collaborators, "Global, regional, and national incidence, prevalence, and years lived with disability for 328 diseases and injuries for 195 countries, 1990-2016: a systematic analysis for the Global Burden of Disease Study 2016," Lancet, Sep. 2017, 390(10100):1211-1259.
Gharpure et al., "Cryptosporidiosis outbreaks—United States, 2009-2017," MMWR Morb. Mortal Wkly. Rep., Jun. 2019, 68(25):568-572.
He et al., "Vitrification by ultra-fast cooling at a low concentration of cryoprotectants in a quartz micro-capillary: a study using murine embryonic stem cells," Cryobiology, Jun. 2008, 56(3):223-232, 24 pages.
Heo et al., ""Universal" vitrification of cells by ultra-fast cooling," Technology (Singap World Sci), Mar. 2015, 3(1):64-71, 18 pages.
Hopkins et al., "Effect of common cryoprotectants on critical warming rates and ice formation in aqueous solutions," Cryobiology, Dec. 2012, 65(3):169-178, 25 pages.
International Preliminary Report on Patentability in International Appln. No. PCT/US2021/023329, mailed on Sep. 29, 2022, 8 pages.
International Search Report & Written Opinion in International Appln. No. PCT/US2021/023329, mailed on Jun. 28, 2021, 10 pages.
Jaskiewicz et al., "Cryopreservation of infectious cryptosporidium parvum oocysts," Nat. Commun., Jul. 2018, 9:2883, 8 pages.
Jenkins et al., "Significance of wall structure, macromolecular composition, and surface polymers to the survival and transport of Cryptosporidium parvum oocysts," Appl Environ Microbiol., Mar. 2010, 76(6):1926-1934.
Khalil et al., "Morbidity, mortality, and long-term consequences associated with diarrhoea from Cyptosporidium infection in children younger than 5 years: a meta-analyses study," Lancet Glob. Health, Jul. 2018, 6(7):e758-e768.

(Continued)

*Primary Examiner* — Robert J Yamasaki
*Assistant Examiner* — Trevor Kane
(74) *Attorney, Agent, or Firm* — Fish & Richardson P.C.

(57) ABSTRACT

Methods of bulk cryopreservation of *C. parvum* oocysts by vitrification using high aspect ratio cryopreservation devices are disclosed. Cryopreserved oocysts exhibit high viability, maintain infectivity in vitro, and are infectious to inter-feron-γ knockout mice. The course of the infection is comparable to that observed with unfrozen oocysts.

18 Claims, 12 Drawing Sheets

(56) References Cited

OTHER PUBLICATIONS

Kotloff et al., "Burden and aetiology of diarrhoeal disease in infants and young children in developing countries (the Global Enteric Multicenter Study, GEMS): a prospective, case-control study," Lancet, Jul. 2013, 382(9888):209-222, 14 pages.

Kuwayama et al., "Highly efficient vitrification method for cryopreservation of human oocytes," Reprod Biomed Online, Sep. 2005, 11(3):300-308.

Lee et al., "Ultra-rapid vitrification of mouse oocytes in low cryoprotectant concentrations," Reprod Biomed Online, Feb. 2010, 20(2):201-208.

Martino et al., "Development into blastocysts of bovine oocytes cryopreserved by ultra-rapid cooling," Biol Reprod., May 1996, 54(5):1059-1069.

Mølbak et al., "Cryptosporidiosis in infancy and childhood mortality in Guinea Bissau, West Africa," BMJ, 1993, 307:417-420.

Okhuysen et al., "Infectivity of a Cryptosporidium parvum isolate of cervine origin for healthy adults and interferon-gamma knockout mice," J Infect. Dis., May 2002, 185(9):1320-1325.

Robertson et al., "Survival of Cryptosporidium parvum oocysts under various environmental pressures," Appl Environ Microbiol., Nov. 1992, 58(11):3494-3500.

Sherwood et al., "Experimental cryptosporidiosis in laboratory mice," Infect Immun., Nov. 1982, 38(2):471-475.

Tzipori and Widmer, "A hundred-year retrospective on cryptosporidiosis," Trends Parasitol., Apr. 2008, 24(4):184-189, 11 pages.

Vande Burgt et al., "Comparison of in vitro viability methods for Cryptosporidium oocysts," Exp. Parasitol., Apr. 2018, 187:30-36, 23 pages.

Widmer et al., "Genotypic and phenotypic characterization of Cryptosporidium parvum isolates from people with AIDS," J. Infect. Dis., Sep. 1998, 178(3):834-840.

* cited by examiner

- Bleach 5%, 0.5 M Trehalose/ 30% DMSO
- Bleach 5%, 0.8 M Trehalose/ 50% DMSO
- Bleach 20%, 0.5 M Trehalose/ 30% DMSO
- Bleach 20%, 0.8 M Trehalose/ 50% DMSO

HIGH ASPECT RATIO DEVICES AND METHODS FOR VITRIFICATION OF BIOLOGICAL SAMPLES BY RAPID COOLING

CLAIM OF PRIORITY

This application is a U.S. National Phase Application under 35 U.S.C. § 371 of International Patent Application No. PCT/US2021/023329, filed on Mar. 19, 2021, which claims the benefit of U.S. Provisional Patent Application No. 62/992,413, filed on Mar. 20, 2020, each of which are incorporated by reference herein in its entirety.

STATEMENT OF FEDERALLY SPONSORED RESEARCH

This invention was made with government support under Grant No. AI154026, awarded by National Institutes of Health. The government has certain rights in the invention.

FIELD

The subject matter disclosed herein generally relates to devices and methods for vitrification of cells.

BACKGROUND

Infection with protozoa of the genus *Cryptosporidium* is a leading cause of child morbidity and mortality associated with diarrhea in the developing world. Research on this parasite has been impeded by many technical limitations, including the lack of cryopreservation methods. While cryopreservation of *Cryptosporidium* oocysts by vitrification can be achieved, the method is restricted to small sample volumes of only 2 μL, thereby limiting the usefulness of this procedure. It is therefore of interest to develop new methods and devices for vitrification of large sample volumes of *Cryptosporidium* oocysts, which will aid research efforts on this parasite, for example, by enabling the sharing of isolates among different laboratories and the standardizing of clinical trials.

SUMMARY OF THE INVENTION

The present disclosure is based, at least in part, on the development of methods and devices for vitrification of cells that provide several improvements over conventional approaches. Such improvements include:

(a) Increased sample volume resulting, at least in part, from design of vitrification cassettes that are capable of holding large sample volumes with minimal reduction of the cooling rate. Using parasites in the oocyst stage as an example, the vitrification cassettes described herein enabled cryopreservation of a 100-fold increase in sample volume compared to a previously reported microcapillary.

(b) Increased viability and infectivity of cryopreserved cells resulting, at least in part, from increased uptake of cryoprotective agents using permeabilization and dehydration conditions described herein.

(c) Reduced toxicity and increased intracellular concentrations of cryoprotective agents achieved by adding cryoprotective agents in a step-wise manner rather than all at once as reported in previous methods.

(d) Lower cost for manufacturing of vitrification cassettes described herein compared to previously reported specimen containers due at least in part to high volume production of the vitrification cassettes using existing reel-to-reel manufacturing processes and low-cost laminates and adhesives.

Accordingly, aspects of the present disclosure provide vitrification cassettes and methods of use thereof for cryopreserving large sample volumes without substantial loss of cell viability or cell activity.

The present disclosure provides, in some embodiments, methods for high-volume cryopreservation of a plurality of cells by vitrification comprising: (a) incubating the cells in a vitrification solution comprising a dehydrating agent for a time and under conditions sufficient to dehydrate the cells; (b) adding one or more cryoprotective agents to the vitrification solution and incubating the cells in the vitrification solution for a time and under conditions sufficient for uptake of the cryoprotective agent by the cells; (c) increasing a total concentration of the one or more cryoprotective agents in the vitrification solution by at least 10% and loading the cells in the vitrification solution into a high aspect ratio vitrification cassette, wherein the vitrification cassette comprises: a bottom layer; a top layer; an intermediate layer disposed between the bottom layer and the top layer and enclosing a chamber within the intermediate layer, wherein a volume of the chamber is 50 μL to 500 μL and the outer dimensions of the chamber are 40 to 65 mm by 15 to 45 mm; and at least one port fluidly connected to the chamber, wherein the bottom, the intermediate, and the top layers are laminated together; and (d) cooling the cells in the vitrification solution in the vitrification cassette to a temperature less than or equal to a glass transition temperature of the vitrification solution at a rate equal to or greater than 100,000° C./minute, wherein the cooling causes vitrification of the plurality of cells.

In some embodiments, the dehydrating agent is a salt, a sugar, or a combination thereof. In some embodiments, the sugar is sucrose, trehalose, raffinose, stachyose, dextran, or a combination thereof. In some embodiments, the concentration of the dehydrating agent in the vitrification solution decreases from step (b) to step (c) and from step (c) to step (d). In some embodiments, the concentration of the dehydrating agent in the vitrification solution is 0.5 to 2.5 M.

In some embodiments, the one or more cryoprotective agents are selected from the group consisting of glycerol, ethylene glycol, 1,2-propanediol, and dimethyl sulfoxide (DMSO). In some embodiments, step (c) comprises increasing the total concentration of the one or more cryoprotective agents in the vitrification solution by at least 15%. In some embodiments, the concentration of the combination of all cryoprotective agents in the vitrification solution in step (b) is between 25 to 35% (v/v). In some embodiments, the concentration of the combination of all cryoprotective agents in the vitrification solution in step (c) is between 45 to 55% (v/v).

In some embodiments, the cells are cooled by submerging at least a portion of the vitrification cassette into liquid nitrogen. In some embodiments, the cells in the vitrification solution are cooled at a rate equal to or greater than 250,000° C./minute.

In some embodiments, methods further comprise, prior to step (a), exposing the cells to a permeabilization solution comprising a permeabilizing agent for a time and under conditions sufficient to increase uptake of the cryoprotective agent by the cells compared to uptake of the cryoprotective agent by untreated cells. In some embodiments, methods further comprise washing the cells with a wash buffer following exposure of the cells to the permeabilization solution. In some embodiments, the permeabilizing agent is hypochlorite. In some embodiments, the concentration of the permeabilizing agent in the permeabilization solution is 10 to 30% (v/v).

In some embodiments, methods further comprise, after step (d), storing the vitrification cassette at a temperature of at least −80° C. In some embodiments, methods further comprise, after step (d), centrifuging the vitrification cassette, wherein at least a portion of the vitrification cassette is placed in a collection tube for collecting the cells.

In some embodiments, the vitrification cassette comprises two ports, each of which are fluidly connected to the chamber, and placing the cells in the vitrification solution in the vitrification cassette comprises loading the cells onto the first port and aspirating the cells into the sample chamber via the second port.

In some embodiments, the volume of vitrification solution placed into the chamber of the vitrification cassette is between 50 to 500 μL.

In some embodiments, the concentration of the cells in the vitrification solution is between 5,000 to 100,000 cells/μL.

In some embodiments, the level of an activity of the cells after vitrification is at least 50% of that of untreated cells. In some embodiments, the activity is viability, infectivity, or both.

In some embodiments, the cells are selected from the group consisting of eukaryotic cells and prokaryotic cells. In some embodiments, the eukaryotic cells are animal cells, plant cells, fungal cells, or protists. In some embodiments, the animal cells are embryo cells, stem cells, zygote cells, or oocytes. In some embodiments, the protists are parasites selected from the group consisting of Coccidia, *Cyclospora*, *Cryptosporidium*, and *Toxoplasma gondii*. In some embodiments, the species of *Cryptosporidium* is selected from the group consisting of *Cryptosporidium andersoni, Cryptosporidium tyzzeri, Cryptosporidium parvum, Cryptosporidium muris, Cryptosporidium hominis, Cryptosporidium wrairi, Cryptosporidium felis, Cryptosporidium canis, Cryptosporidium baileyi, Cryptosporidium meleagridis, Cryptosporidium galli, Cryptosporidium serpentis, Cryptosporidium saurophilum*, and *Cryptosporidium molnari*. In some embodiments, the parasite is in the form of an infectious oocyst.

In some embodiments, methods further comprise sealing the at least one port with a polymeric seal or an adhesive seal.

Aspects of the present disclosure provide high aspect ratio vitrification cassettes comprising: a bottom layer; a top layer; an intermediate layer disposed between the bottom layer and the top layer and enclosing a chamber within the intermediate layer, wherein a volume of the chamber is 50 μL to 500 μL and the outer dimensions of the chamber are 45 to 65 mm by 15 to 45 mm; and at least one port fluidly connected to the chamber, wherein the bottom, the intermediate, and the top layers are laminated together.

In some embodiments, the bottom and the top layers are laminated together with an adhesive, which is the middle layer. In some embodiments, the bottom and the top layers are laminated together with heat. In some embodiments, the bottom and the top layers are made from a polymeric material. In some embodiments, the bottom and the top layers are made from a polymeric material and the intermediate layer comprises an adhesive material. In some embodiments, the polymeric material is polycarbonate, polymethylmethacrylate, or polypropylene. In some embodiments, the top layer and the bottom layer are the same material.

In some embodiments, at least one of the bottom, the intermediate, and the top layers are made of a material having a thermal conductivity of at least 0.2 W m⁻¹ K⁻¹. In some embodiments, at least one of the bottom, the intermediate, and the top layers are made of a material having a thermal conductivity of at least 5 W m⁻¹ K⁻¹. In some embodiments, the top layer and the bottom layer have the same thermal conductivity.

In some embodiments, each of the bottom layer and the top layer has a thickness between 100 to 500 μm. In some embodiments, the thickness of each of the bottom layer and the top layer is between 160 to 200 μm. In some embodiments, the height of the chamber is between 50 to 150 μm.

In some embodiments, the chamber holds a volume of solution between 150 to 250 μL. In some embodiments, the chamber has a surface area of 2,500 to 10,000 mm². In some embodiments, the outer dimensions of the sample chamber are 45 to 55 mm by 35 to 45 mm.

In some embodiments, the outer dimensions of the sample chamber are 55 to 65 mm by 15 to 25 mm. In some embodiments, the chamber has a ratio of surface area to volume of 0.1 to 1 mm⁻¹. In some embodiments, the chamber forms a serpentine shape.

In some embodiments, the at least one port is sealed with a polymeric seal or an adhesive seal. In some embodiments, the polymeric seal or the adhesive seal is penetrable by a needle. In some embodiments, the polymeric seal or the adhesive seal is in the form of a plug, a sheet, or a gasket. In some embodiments, the at least one port has a diameter between 1 to 5 mm. In some embodiments, the vitrification cassette comprises two ports, each of which are fluidly connected to the chamber.

In some embodiments, vitrification cassettes described herein further comprise at least one channel that is fluidly connected to the chamber. In some embodiments, the vitrification cassette has a thickness of 400 μm to 1 mm.

As used herein, the term "channel" refers to a gap through which fluid may flow. A channel may be a capillary or a conduit wherein aqueous fluids are confined.

As used herein, the term "cryoprotective agent," "cryoprotectant," or "CPA" refers to a compound used to slow or prevent ice nucleation, ice crystal growth, ice formation, or any combination thereof. Cryoprotectants are generally agents with high water solubility and low toxicity. Included within this term are both permeating (e.g., glycerol, ethylene glycol, 1,2-propanediol, and DMSO) and non-permeating (e.g., sugars, dextran, polyvinyl pyrrolidone and hydroxyethyl starch) cryoprotectants. Non-limiting examples of cryoprotectants for use in methods described herein are ethylene glycol, glycerol, 1,2-propanediol, DMSO, and sugars (e.g., sucrose, trehalose, raffinose, stachyose, and dextran).

As used herein, the term "dehydrating agent" refers to a compound that increases the diffusion of water out of cells. Non-limiting examples of dehydrating agents for use in methods described herein include sugars (e.g., sucrose, trehalose, raffinose, stachyose, dextran, sorbitol), salts (e.g., sodium chloride), and combinations thereof.

As used herein, the term "high volume" or "high sample volume" refers to sample volumes of at least 50 μL, at least 100 μL, at least 250 μL, at least 500 μL, or more. In some examples, a high volume or a high sample volume is a sample volume that is greater than the sample volume in a known method for cryopreservation by at least 2-fold, at least 5-fold, at least 10-fold, at least 50-fold, at least 100-fold, or more.

As used herein, the term "permeabilizing agent" refers to a compound that punctures the cell membrane. Non-limiting examples of dehydrating agents for use in methods described herein include strong bases (e.g., hypochlorite), organic solvents (e.g., methanol, acetone), detergents (e.g., saponin, Triton X-100, Tween-20), and combinations thereof.

As used herein, the term "permeabilizing solution" refers to a solution that includes a permeabilizing agent. The permeabilizing solution is mixed with cells prior to vitrification to permeabilize the oocyst membrane, thereby allowing uptake of the one or more cryoprotective agents.

As used here, "thermal conductivity" refers to the intensive property of a material that indicates its ability to conduct heat and is measured in $W\ m^{-1}\ K^{-1}$. Thermal conductivity (k) is defined as the quantity of heat, Q, transmitted in time, t, through a thickness r, in a direction normal to a surface of area A, due to a temperature difference, $\Delta T$, under steady state conditions and when the heat transfer is dependent only on the temperature gradient. Thermal conductivity=heat flow rate distance/(area temperature difference) or $$k = \frac{Q}{t} \times \frac{\tau}{A \times \Delta T}$$

For vitrification cassettes as described herein, the material of any of the top, bottom, or intermediate layers can have a high thermal conductivity.

As used herein, the term "vitrification" refers to a process of converting a material into a glass-like amorphous solid which is free of any crystalline structure. Vitreous solidification occurs at the glass transition temperature (which is lower than the melting temperature, $T_m$, due to supercooling).

As used herein, the term "vitrification cassette" refers to a high aspect ratio container for vitrification of cells. Non-limiting examples of vitrification cassettes are shown in FIGS. 1A-1B and FIGS. 7A-7B.

As used herein, the term "aspect ratio" refers to the ratio of the length of the vitrification cassette to its diameter. In some examples, the aspect ratio refers to the ratio of the length of the chamber of the vitrification cassette to the diameter of the chamber.

As used herein, the term "high aspect ratio" when applied to a vitrification cassette as described herein means that the vitrification cassette has an aspect ratio>1.

As used herein, the term "vitrification solution" refers to a solution that is mixed with the cells prior to vitrification. Vitrification solutions can include, for example, PBS or any physiological solutions. A vitrification solution can be supplemented with one or more components including, but not limited to, serum, proteins, penicillin/streptomycin, lipids, salts, formamide, methoxylated compounds, polymers (e.g., polyvinyl pyrrolidone and polyvinyl alcohol), cryoprotective agent, and dehydrating agents (e.g., sugars).

As used herein, the term "(v/v)" refers to the concentration of solute expressed as a volume percentage, e.g., the concentration 1% (v/v) refers to a solution with 1 ml of solute (e.g., the cryoprotective agent) dissolved in a 100 ml of solution, which includes both the solute (e.g., the cryoprotective agent) and the solvent (e.g., the vitrification solution).

As used herein, the term "cryopreservation" refers to the process of cooling cells either by slow-freezing or vitrification.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

Various aspects and embodiments will be described with reference to the following figures. The figures are not necessarily drawn to scale.

FIG. 3B is a graph showing oocyst viability determined by PI exclusion, both pre-freeze and after thawing of oocysts at different ages. Horizontal lines indicate mean and error bars standard deviation (n=4). There were no differences in pre-freeze and thawed (post-freeze) viability between oocysts of different ages (Kruskal-Wallis test, pre-freeze: p=0.64; post-freeze: p=0.06), except a slight decrease in viability after thawing for 12-week-old oocysts in comparison to 1-week-old oocysts (Mann-Whitney test, *p=0.03).

Figure 4A:
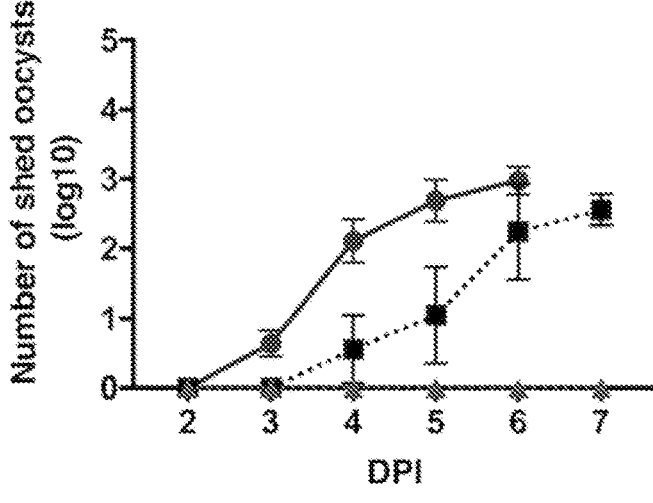
Figure 4B:
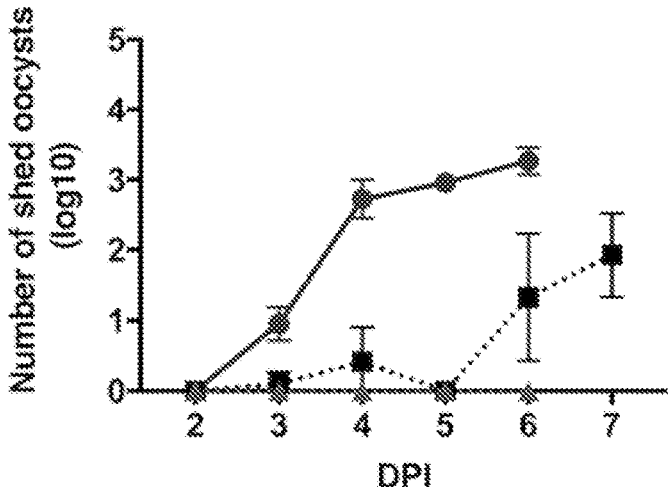
Figure 4C:
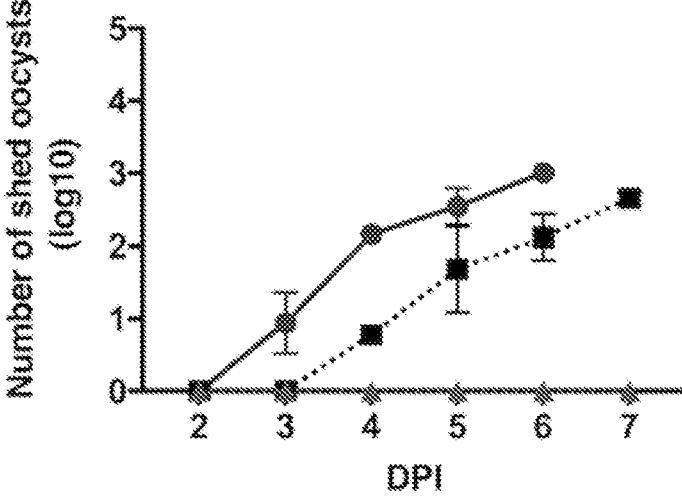

FIGS. 4A-4C are graphs showing that oocysts frozen at the age 2-weeks (FIG. 4A), 6-weeks (FIG. 4B), and 12-weeks (FIG. 4C) using vitrification cassettes after application of the two-step DMSO loading procedure described herein were infectious to IFN-γ knockout mice (transformed data). Fresh oocysts control (circles); oocysts cryopreserved as described herein (square); and heat-inactivated negative control oocysts (triangle).

Figure 5A:
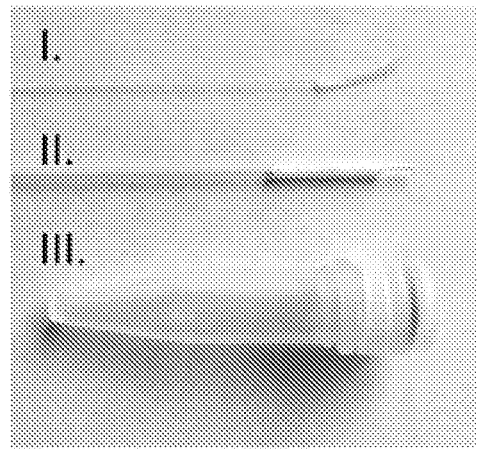

FIG. 5A is an image showing commercially available specimen container including a microcapillary (I), an insemination straw (II), and a cryovial (III).

Figure 5B:
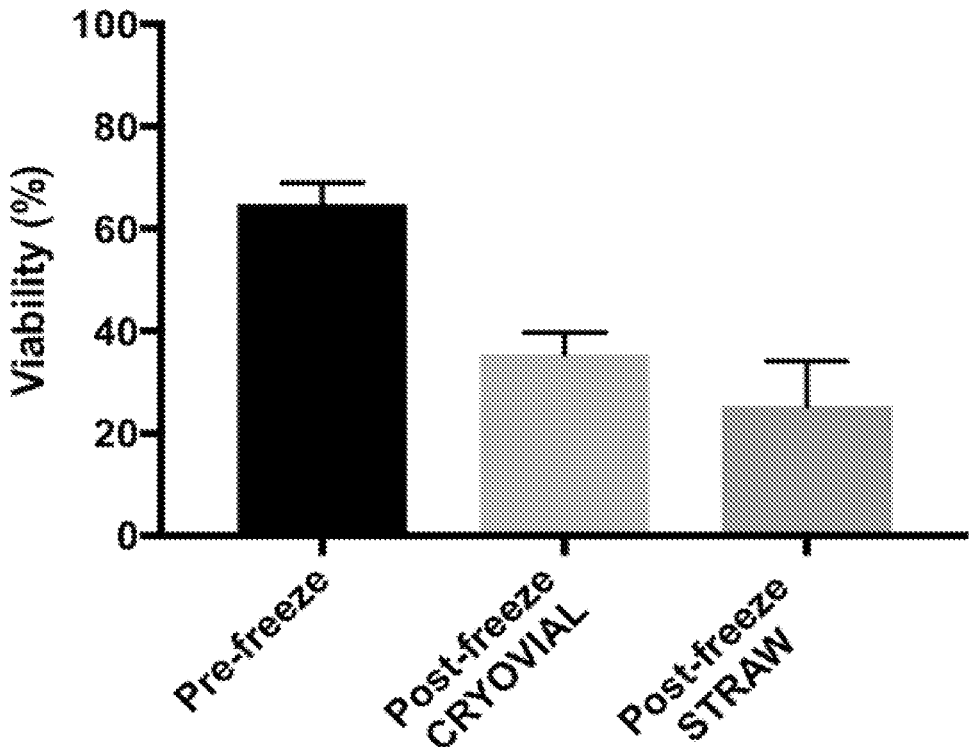

FIG. 5B is a graph showing viability measured by propidium iodide (PI) exclusion after incubation of oocysts with a cocktail of 40% DMSO/6% PVP for 5 min, without freezing (CPA toxicity control) or after thawing in liquid nitrogen using a cryovial or an insemination straw (n=3).

Figure 5C:
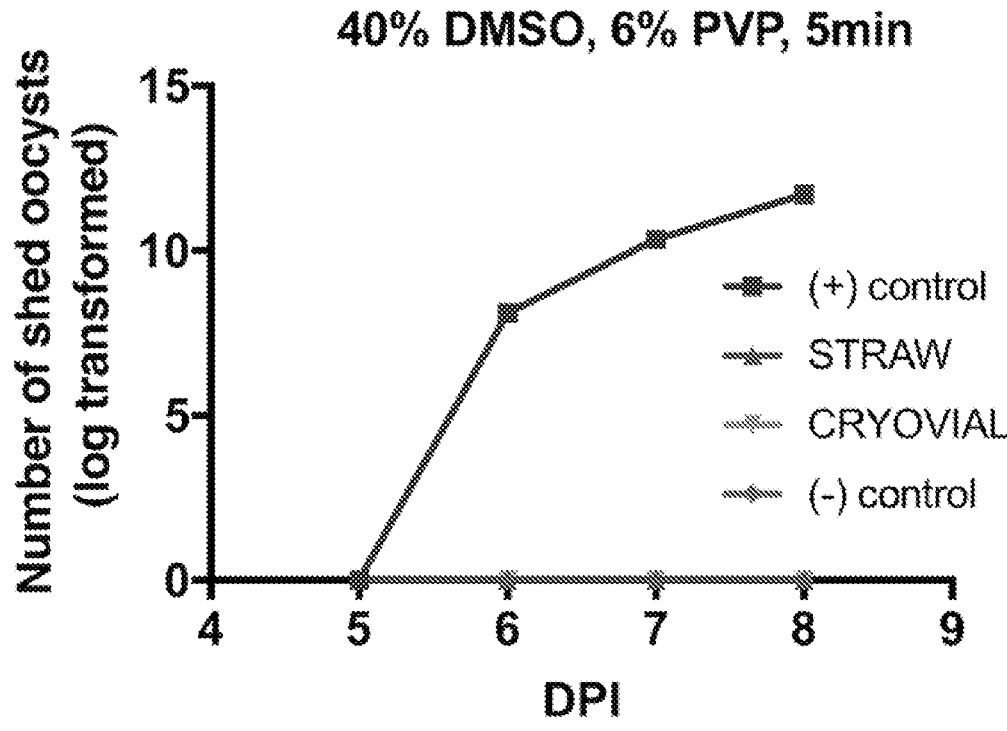

FIG. 5C is a graph showing infectivity of oocysts cryopreserved in commercially available specimen containers to interferon-gamma (IFN-γ) knockout mice (n=3, mice were inoculated orally with 5,000 PI-oocysts). Positive (unfrozen) and negative (heat-inactivated) oocyst treatments were included as matched controls.

Figure 6A:
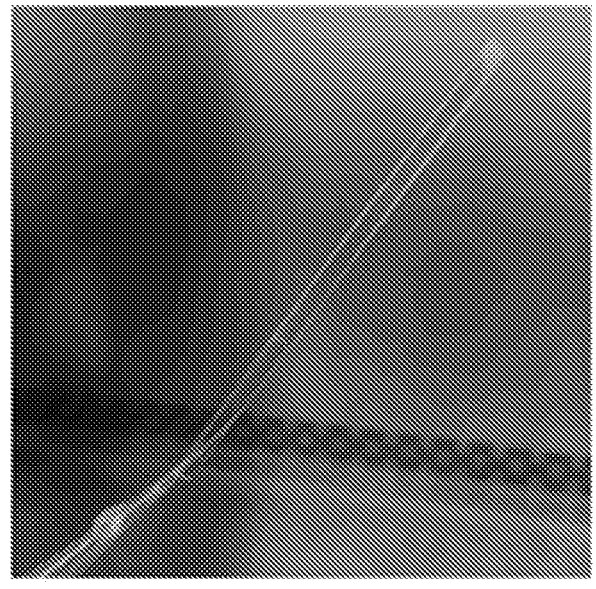

FIG. 6A is an image of oocysts cryopreserved in a rectangular capillary after one-step addition of 50% DMSO (5 min incubation).

Figure 6B:
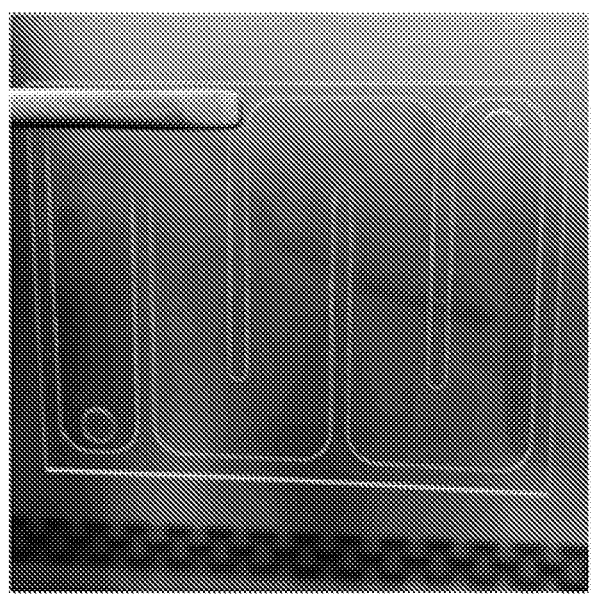

FIG. 6B is an image of oocysts cryopreserved in a vitrification cassette after one-step addition of 50% DMSO (5 min incubation).

Figure 6C:
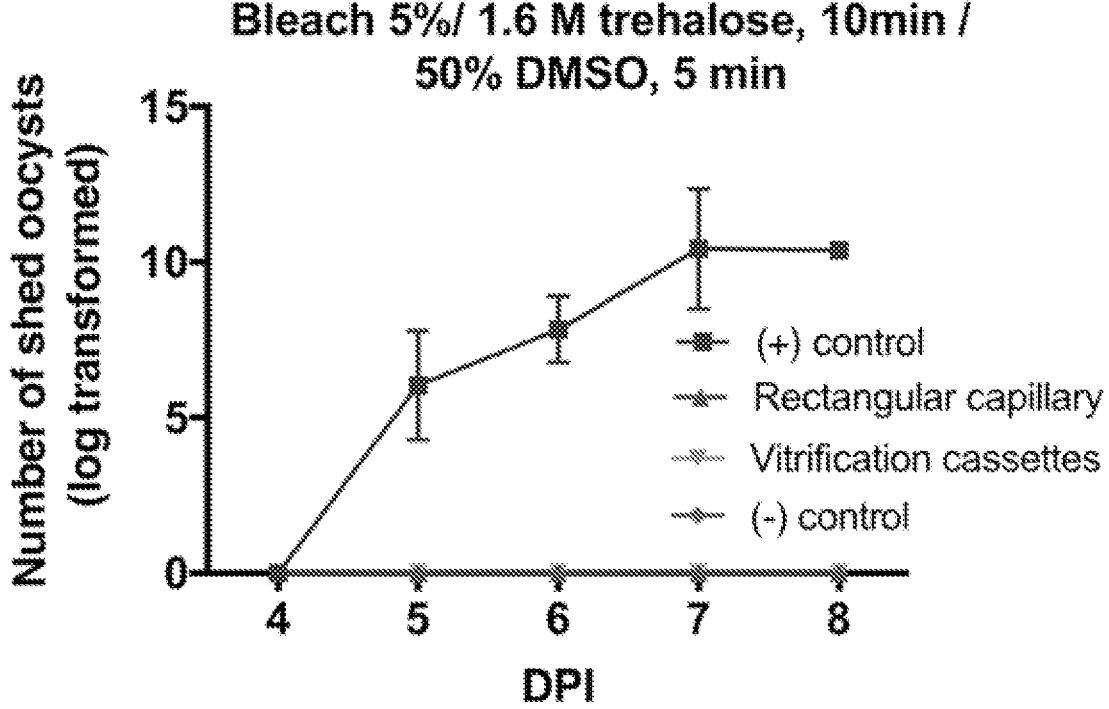
Figure 7A:
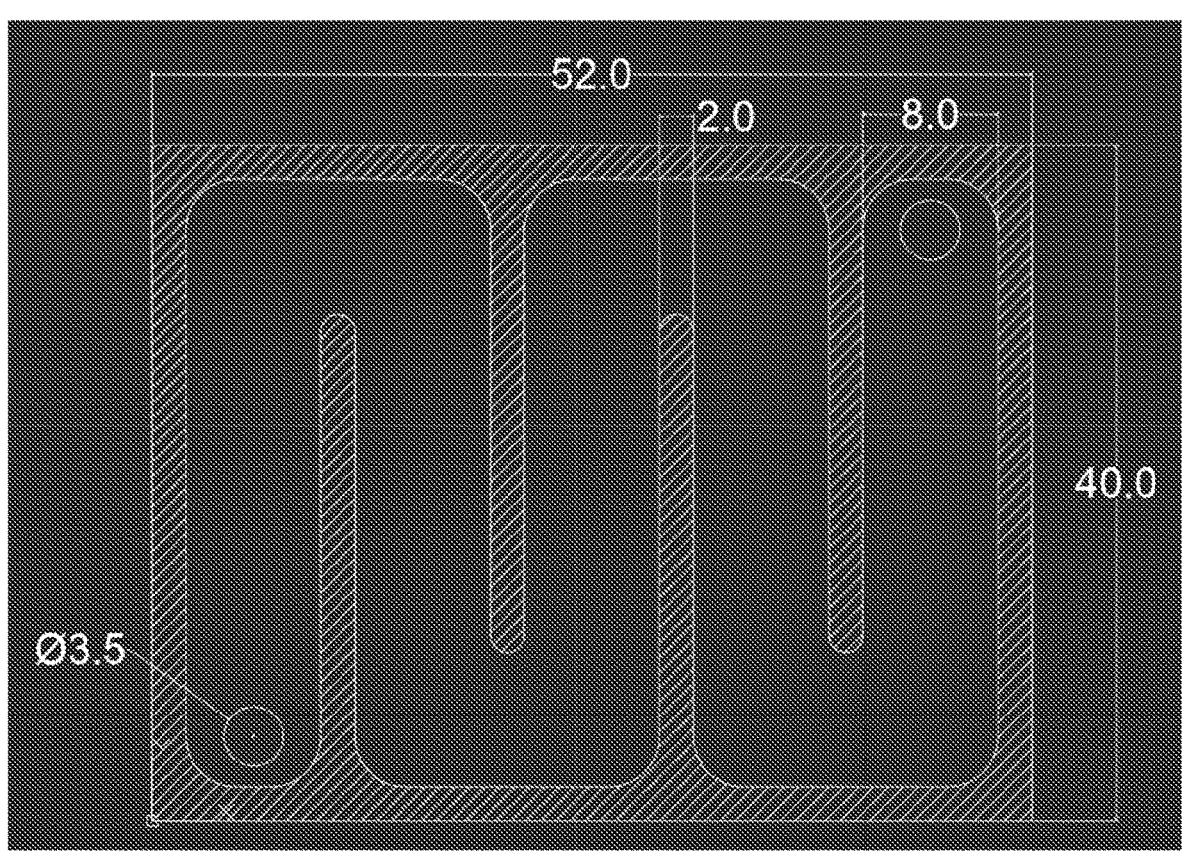

FIG. 6C is a graph showing infectivity of oocysts cryopreserved in a rectangular capillary or a vitrification cassette to interferon-gamma (IFN-γ) knockout mice. Mice were inoculated orally with 10,000 PI-oocysts. Unfrozen and heat-inactivated oocysts were included as matched positive and negative control, respectively FIG. 7A is a drawing showing dimensions of an example of a vitrification cassette in millimeters.

Figure 7B:
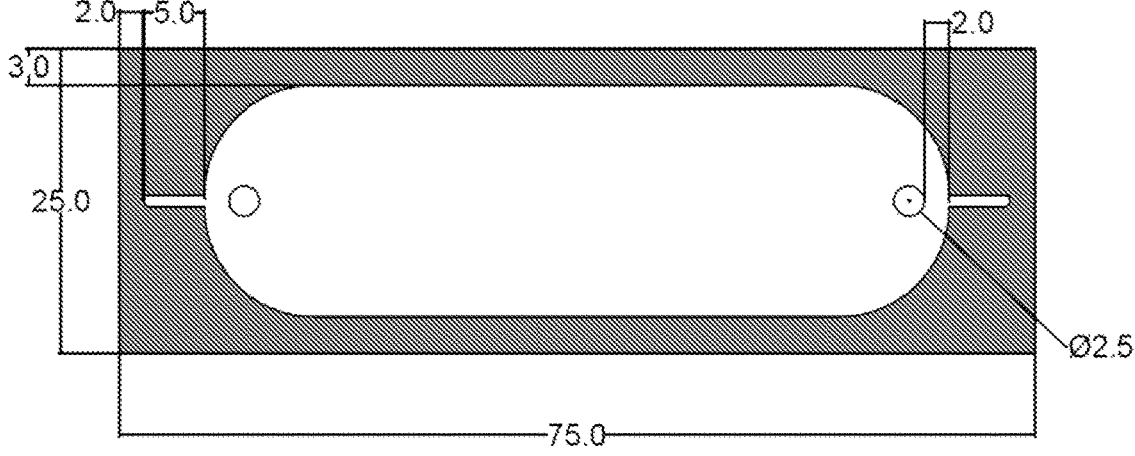

FIG. 7B is a drawing showing dimensions of an example of a vitrification cassette in millimeters.

Figure 8A:
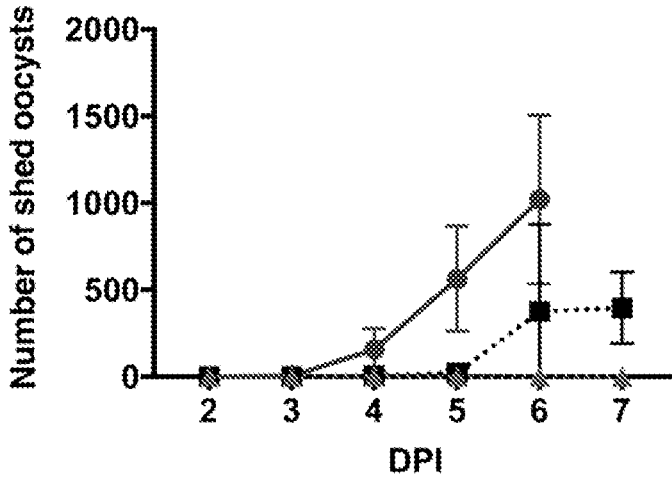
Figure 8B:
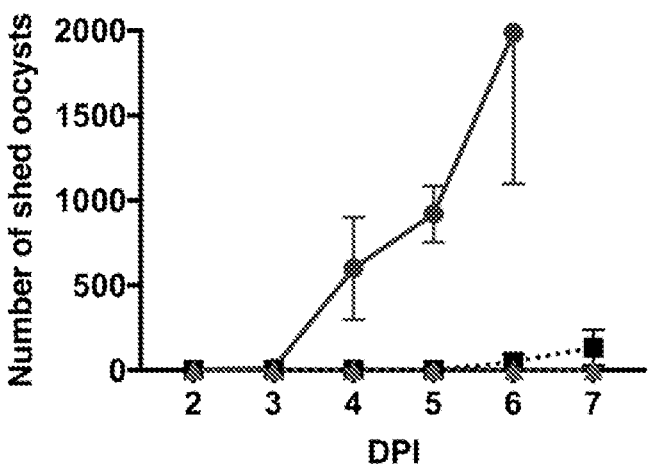
Figure 8C:
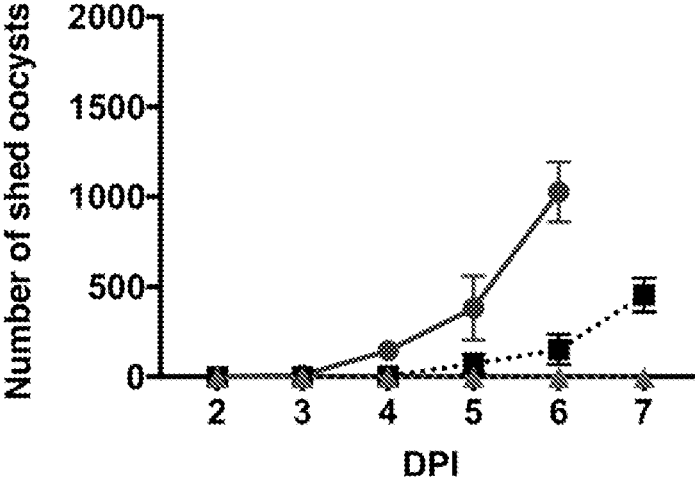

FIGS. 8A-8C are graphs showing that oocysts frozen at the age 2-weeks (FIG. 8A), 6-weeks (FIG. 8B), and 12-weeks (FIG. 8C) using vitrification cassettes after application of the two-step DMSO loading procedure described herein were infectious to IFN-γ knockout mice (untransformed data). Fresh oocysts control (circles); oocysts cryopreserved as described herein (square); and heat-inactivated negative control oocysts (triangle).

The details of one or more embodiments of the invention are set forth in the description below. Other features or advantages of the present invention will be apparent from the following drawings and detailed description of several embodiments, and also from the appended claims.

DETAILED DESCRIPTION

The present disclosure is based, at least in part, on the development of methods and devices for high-volume cryopreservation of cells by vitrification that increased the volume of a single cryopreserved sample of *Cryptosporidium* oocysts by 100-fold compared to known techniques such as those involving microcapillaries.

Cryptosporidiosis is a leading cause of diarrheal disease and infant death in low- and middle-income countries. The Global Enteric Multicenter Study identified infection with *Cryptosporidium* parasites as the second most common cause of moderate-to-severe diarrhea in infants in Sub-Saharan Africa and South-East Asia (Kotloff et al., Burden and aetiology of diarrhoeal disease in infants and young children in developing countries (the Global Enteric Multicenter Study, GEMS): a prospective, case-control study. *Lancet* 382, 209-222 (2013). In this setting, cryptosporidiosis is strongly associated with death of infants and toddlers (Kotloff et al., Burden and aetiology of diarrhoeal disease in infants and young children in developing countries (the Global Enteric Multicenter Study, GEMS): a prospective, case-control study. *Lancet* 382, 209-222 (2013); Molbak et al., Cryptosporidiosis in infancy and childhood mortality in Guinea Bissau, west Africa. *BMJ* 307, 417-420 (1993)). In fact, acute cryptosporidiosis caused >48,000 deaths among children below the age of five in 2016 alone, according to the Global Burden of Disease Study (Global, regional, and national incidence, prevalence, and years lived with disability for 328 diseases and injuries for 195 countries, 1990-2016: a systematic analysis for the Global Burden of Disease Study 2016. *Lancet* 390, 1211-1259 (2017)). Long-term consequences of early childhood cryptosporidiosis are related to malabsorption and undernutrition and include cognitive impairment and stunted growth (Checkley et al., Effects of *Cryptosporidium parvum* infection in Peruvian children: growth faltering and subsequent catch-up growth. *Am. J. Epidemiol.* 148, 497-506 (1998); Guerrant et al., Association of early childhood diarrhea and cryptosporidiosis with impaired physical fitness and cognitive function four-seven years later in a poor urban community in northeast brazil. *Am. J. Trop. Med. Hyg.* 61, 707-713 (1999)). It is estimated that burden from cryptosporidiosis, adjusted for undernutrition, accounted for more than 12 million disability-adjusted life—years in 2016 (Khalil et al., Morbidity, mortality, and long-term consequences associated with diarrhoea from *Cryptosporidium* infection in children younger than 5 years: a meta-analyses study. *Lancet* Glob. Health 6, e758-e768 (2018)). Additionally, cryptosporidiosis is also a key opportunistic infection among immunocompromised individuals, responsible for life-threatening persistent diarrhea (Tzipori & Widmer, A hundred-year retrospective on cryptosporidiosis. *Trends Parasitol.* 24, 184-189 (2008)). In industrialized countries, prevalence of cryptosporidiosis is on the rise with a 13% increase in the number of outbreaks per year in the USA (Gharpure et al., Cryptosporidiosis outbreaks—United States, 2009-2017. *MMWR Morb. Mortal Wkly. Rep.* 68, 568-572 (2019)).

Current anti-parasitic drugs are ineffective and no vaccine is available to control cryptosporidiosis. This highlights the need to develop vaccines, better therapeutics and diagnostic tools for the disease. Until recently, a major technical limitation to research on cryptosporidiosis was the lack of methods for cryopreserving the parasite. In the absence of such methods, laboratory strains of *Cryptosporidium* are continuously propagated in laboratory animals (e.g., calves, pigs and rodents) every 6-8 weeks. This process is expensive and time-consuming, and has for years limited the sharing of well-characterized isolates among laboratories. This further precludes execution of clinical trials with standardized parasite preparations and hinders the development and evaluation of therapeutics and vaccines.

Scientists have attempted to cryopreserve infectious *Cryptosporidium* oocysts for decades without much success. These poor outcomes may be due in part to insufficient loading of cryoprotective agents (CPAs, e.g., dimethylsulfoxide (DMSO), ethylene glycol). Specifically, the complex tetralaminar oocyst wall shielding sporozoites, the fragile invasive stage of the parasite, also prevents effective CPA loading. Another reason for these poor outcomes may be the toxicity of CPAs, which can compromise the viability and infectivity of oocysts that have been exposed to these toxic agents. Some methods such as vitrification utilize high concentrations of CPAs (~4-8 M), which is combined with rapid cooling rates to achieve formation of an amorphous glassy state that is devoid of ice crystals.

Accordingly, described herein are cryopreservation methods that increase the intracellular concentrations of CPAs while minimizing cytotoxicity to enable increased sample volume through the design and manufacture of novel high aspect ratio specimen containers referred to as "vitrification cassettes." This strategy increases the volume of a single cryopreserved sample by at least 100-fold compared to the previously reported microcapillaries. This volume is sufficient to produce multiple inocula from a single cryopreserved sample (e.g., 4 doses for pigs or >20 human doses for clinical trials), thus overcoming a major bottleneck in the development and testing of therapeutics for the treatment of cryptosporidiosis.

I. High-Volume Cryopreservation Methods

The cryopreservation methods described herein can be used to cryopreserve a high-volume of cells that can later be used in a wide range of downstream applications. For example, the methods can be used to cryopreserve therapeutic cells (e.g., stem cells, T cells), which can then be used for cell-based therapies, cell transplantation, tissue engineering, and regenerative medicine. In another example, the methods can be used to cryopreserve unicellular or multicellular organisms such as parasites (e.g., parasites in the form of infectious oocysts), which can then be used for research and development of therapeutics and diagnostic tools for treating patients infected with such organisms.

To practice the methods described herein, a plurality of cells is mixed with a vitrification solution comprising a dehydrating agent and one or more cryoprotective agents, loaded into a vitrification cassette, and rapidly cooled for a time and under conditions sufficient to cause vitrification of the plurality of cells.

The cells can be added to the vitrification solution or the vitrification solution can be added to the cells. Alternatively, the cell media is modified to include all the components needed for vitrification. The concentration of the cells in the vitrification solution can vary depending on the type of cells and on the downstream use of the cells. For example, for oocysts (e.g., *Cryptosporidium* oocysts) for use in laboratory research and clinical trials, the concentration of cells in the vitrification solution can be between 5,000 to 100,000 cells/μL.

The vitrification solution can include any physiologic solution such as phosphate buffered saline (PBS) or cell media. The vitrification solution can be supplemented with one or more components including, but not limited to, serum, proteins, penicillin/streptomycin, lipids, salts, formamide, methoxylated compounds, polymers (e.g., polyvinyl pyrrolidone and polyvinyl alcohol), cryoprotective agents, dehydrating agents (e.g., sugars, salts, or a combination thereof), or combinations thereof.

Prior to loading into the vitrification cassette, the cells are incubated in a vitrification solution comprising a dehydrating agent under conditions and for a time sufficient to promote dehydration of the cells. For example, when the dehydrating agent is trehalose, the cells are incubated in a vitrification solution comprising 0.5 to 2.5 M trehalose (e.g., 1.6 M trehalose) for 5 to 20 minutes (e.g., 10 minutes) at room temperature.

One or more cryoprotective agents are then added to the vitrification solution and the cells are incubated under conditions and for a time sufficient for uptake (or loading) of the cryoprotective agent by the dehydrated cells.

The total concentration of the one or more cryoprotective agents in the vitrification solution is then increased by at least 10%, at least 15%, at least 20%, at least 25% or more prior to loading the cells in the vitrification solution into the vitrification cassette. Without wishing to be bound by theory, the concentration of the one or more cryoprotective agents within the cells increases as a result of water loss caused by the osmotic gradient applied during the second addition of the one or more cryoprotective agents.

Accordingly, methods described herein comprise step-wise addition of the one or more cryoprotective agents. For example, when the one or more cryoprotective agents is DMSO, a stock solution of DMSO is added to the vitrification solution to achieve a concentration of 25% to 35% v/v DMSO/vitrification solution, and then the cells are incubated for 5 to 10 minutes at room temperature. Following incubation, the concentration of DMSO in the vitrification solution is increased to 45% to 55% v/v DMSO/vitrification solution, and then the cells in the vitrification solution are loaded into the vitrification cassette. When using multiple cryoprotective agents, the concentration of the combination of all cryoprotective agents in the vitrification solution during step-wise addition of the one or more cryoprotective agents is between 25 to 35% (v/v) for the first step and between 45 to 55% (v/v) for the second step.

In some examples, the step-wise addition of the one or more cryoprotective agents decreases the concentration of the dehydrating agent in the vitrification solution. For example, when the dehydrating agent is trehalose, the concentration of the trehalose in the vitrification solution is decreased by the first addition of the one or more cryoprotective agents (e.g., the concentration of trehalose is decreased from 1.6 M to 0.8 M) and then further decreased by the second addition of the one or more cryoprotective agents (e.g., the concentration of trehalose is decreased from 0.8 M to 0.5 M).

Methods described herein also include treating the cells with a permeabilizing agent to increase uptake of the cryoprotective agent. Such methods are useful for cells that have an impermeable nature such as oocysts, which have an oocyst wall that is resistant to mechanical and chemical damage.

In such instances, prior to incubating the cells in the vitrification solution, the cells are exposed to a permeabilization solution comprising a permeabilizing agent for a time and under conditions sufficient to increase uptake of the cryoprotective agent by the cells compared to uptake of the cryoprotective agent by untreated cells. For example, the cells are exposed to 10% to 30% hypochlorite (e.g., 20% hypochlorite) for 10 seconds to 5 minutes (e.g., 1 minute) on ice, and then washed with PBS.

The cells are loaded into the vitrification cassette, for example, by loading the cells onto the cassette port and aspirating the cells into the cassette via negative pressure created by removing the air from the opposite cassette port. In some examples, the port(s) is sealed with a polymeric seal or an adhesive seal prior to submerging the vitrification cassette into liquid nitrogen.

The volume of vitrification solution loaded into the chamber of the vitrification cassette can depend on various factors such as the volume of the chamber, the type of cells, the downstream use of the cells, and combinations thereof.

For example, the volume of vitrification solution placed into the chamber of the vitrification cassette is between 50 μL to 10 mL.

In some examples, the volume of vitrification solution placed into the chamber of the vitrification cassette is between 50 to 500 µL, between 50 to 450 µL, between 50 to 400 µL, between 50 to 350 µL, between 50 to 300 µL, between 50 to 250 µL, between 50 to 200 µL, between 50 to 150 µL, between 50 to 100 µL, between 100 to 500 µL, between 150 to 500 µL, between 200 to 500 µL, between 250 to 500 µL, between 300 to 500 µL, between 350 to 500 µL, between 400 to 500 µL, or between 450 to 500 µL.

In some examples, the volume of vitrification solution placed into the chamber of the vitrification cassette is between 500 to 1000 µL, between 600 to 1000 µL, between 700 to 1000 µL, between 800 to 1000 µL, between 900 to 1000 µL, between 500 to 900 µL, between 500 to 800 µL, between 500 to 700 µL, or between 500 to 600 µL.

In some examples, the volume of vitrification solution placed into the chamber of the vitrification cassette is between 1 to 10 mL, between 2 to 10 mL, between 3 to 10 mL, between 4 to 10 mL, between 5 to 10 mL, between 6 to 10 mL, between 7 to 10 mL, between 8 to 10 mL, between 9 to 10 mL, between 1 to 9 mL, between 1 to 8 mL, between 1 to 7 mL, between 1 to 6 mL, between 1 to 5 mL, between 1 to 4 mL, between 1 to 3 mL, or between 1 to 2 mL.

The vitrification cassette is then exposed to temperatures less than or equal to −80° C., e.g., less than or equal to the temperature of liquid nitrogen or slush nitrogen temperature (e.g., −196° C. or −205° C., respectively), and the vitrification solution containing the cells is cooled at a rate equal to or greater than 30,000-1,000,000° C./minute, e.g., 100,000° C./minute, 200,000° C./minute, 300,000° C./minute, or 1,000,000° C./minute. For example, the vitrification cassette or a portion thereof can be plunged into liquid nitrogen or slush or slurry nitrogen, optionally with shaking, to cause vitrification of the cells and the vitrification solution in the absence of ice formation.

The vitrified cells in the vitrification solution can then be stored at a temperature less than or equal to −80° C. (e.g., equal to or less than liquid nitrogen temperature) for any desired amount of time (e.g., up to and beyond 3 months, 6 months, 12 months, or more) until the cells are needed. The cells are then warmed, using any number of techniques known in the art, for example, by plunging the vitrification cassette into a 1×PBS solution at 20-37° C., for example room temperature, optionally with shaking and optionally supplemented with sugar or other CPAs. After warming, the cells are generally washed and treated as needed for the research or clinical applications. It will be clear to the skilled artisan the exact conditions and media that are used for culturing the cells before, during, and after warming. Exemplary protocols are provided in the examples below.

The cells are collected from the vitrification cassette, for example, using hydraulic pressure applied by flushing a solution (e.g., PBS) through the cassette port and collecting the cells expelled through the opposite port. In another example, the cells are collected from the vitrification cassette using centrifugation. In such instances, at least a portion of the vitrification cassette is placed in a collection tube for collecting the cells expelled from the vitrification cassette during centrifugation.

Methods described herein can be used for high-volume cryopreservation of any species and any type of cells. In some examples, the cells include eukaryotic cells (e.g., animal cells, plant cells, fungal cells, or protists) or prokaryotic cells (e.g., bacterial cells). Methods described herein also include cryopreservation of organisms such as parasites, viruses, bacteria, fungi, invertebrates (e.g., insects), fish, or reptiles.

In some examples, the cells include mammalian cells. In such instances, the cells can include differentiated cells such as epithelial cells, cardiomyocytes, neural cells, epidermal cells, keratinocytes, hematopoietic cells, melanocytes, chondrocytes, B-cells, T-cells, erythrocytes, macrophages, monocytes, fibroblasts, or muscle cells or undifferentiated cells such as stem cells (e.g., embryonic, mesenchymal, or adult stem cell), gametocytes, oocytes, sperm, zygotes, or embryos. Other cells that can be cryopreserved using the methods and devices described herein include those from the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

In some examples, the cells include protists such as parasites, e.g., Coccidia, *Cyclospora*, *Cryptosporidium*, and *Toxoplasma gondii*. In such instances, the cells can include any species of parasite, e.g., a species of *Cryptosporidium* such as *Cryptosporidium anderson*, *Cryptosporidium parvum*, *Cryptosporidium muris*, *Cryptosporidium hominis*, *Cryptosporidium wrairi*, *Cryptosporidium felis*, *Cryptosporidium canis*, *Cryptosporidium baileyi*, *Cryptosporidium meleagridis*, *Cryptosporidium galli*, *Cryptosporidium serpentis*, *Cryptosporidium saurophilum*, and *Cryptosporidium molnari*. The cells can include parasites of any stage such as oocyst stage parasites.

The cells can be obtained from any source suitable for harvesting such cells, e.g., from a human, a non-human mammal, or a cell culture. The cells can be obtained using any technique known in the art and maintained in media appropriate for the type of cells.

Various tests are known in the art to determine the viability and function of the cells after warming and these tests are dependent on the cell type and the desired use of the cell. For example, for *Cryptosporidium* oocysts, maintenance of infectivity is important and can be tested using known methods, e.g., MDBK infection assays or infectivity of IFN-γ knockout mice (see Examples below).

The methods described herein cryopreserve large batches (e.g., high sample volumes) without severely compromising viability and activity of the cells. In some examples, the level of activity of the cells after vitrification is at least 50% of the level of activity of untreated cells, e.g., the level of activity of the cells after vitrification is at least 60%, at least 70%, at least 80%, at least 90%, or more of that of untreated cells.

In some examples, at least 20%, at least 30%, at least 40%, at least 50%, at least 60%, at least 70%, at least 80%, at least 90%, at least 90%, or more of the cells are viable (e.g., alive and/or have normal cellular functions) after cryopreservation. In some examples, at least 20%, at least 30%, at least 40%, at least 50%, at least 60%, at least 70%, at least 80%, at least 90%, at least 90%, or more of the cells are infectious after cryopreservation.

II. Vitrification Cassettes

Figure 1A:
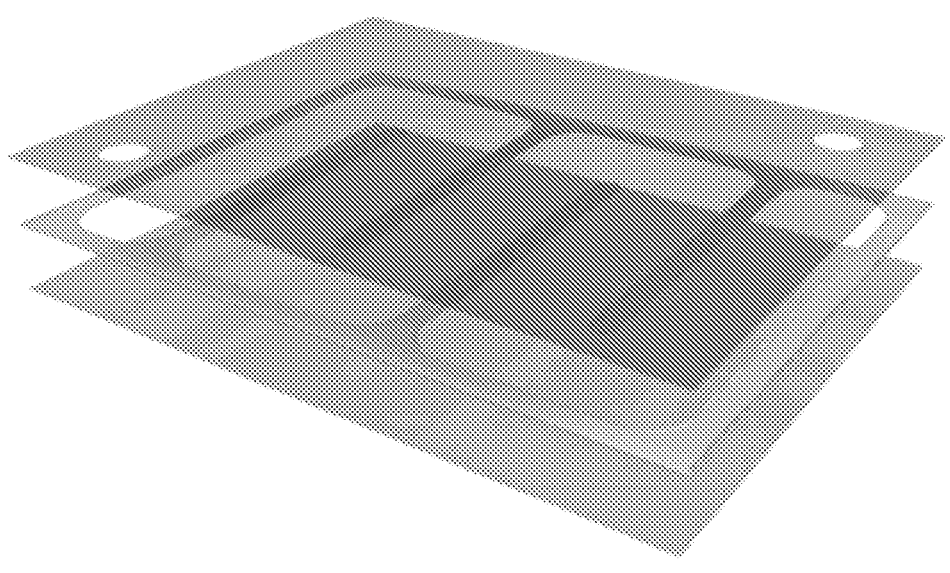
FIG. 1A is a schematic depiction of an example of a vitrification cassette.
Figure 1B:
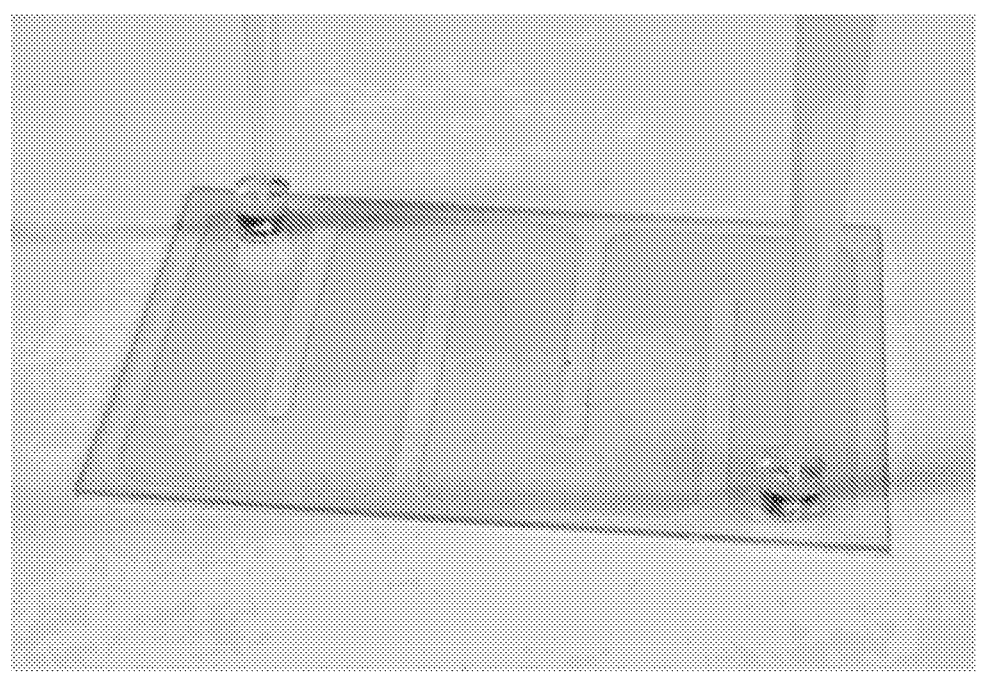
FIG. 1B is an image showing loading of a vitrification cassette via a pipette tip affixed to a port.

Also provided herein are vitrification cassettes for cryopreservation of large batches (e.g., high sample volumes) of cells such as oocysts. FIGS. 1A-1B illustrate an example of a vitrification cassette described herein.

As shown in FIG. 1A, the vitrification cassette, in some embodiments, includes three layers: a bottom layer, a top layer, and an intermediate layer disposed between the bottom layer and the top layer and enclosing a chamber for holding the cells in the vitrification solution. The top layer includes two openings or ports that are fluidly connected to the chamber, thereby allowing loading of the cells into the chamber. The three layers are laminated together to form the vitrification cassette shown in FIG. 1B.

The layers of the vitrification cassette can be laminated together using any method known in the art. In some examples, the layers can be laminated together with an adhesive (e.g., an epoxy or a pressure sensitive adhesive). In some examples, the adhesive is the middle layer between the top and bottom layers. In some examples, the layers can be laminated together with heat. Alternatively, or in addition to, the layers can be mechanically held together, e.g., the layers can be bolted or clamped together.

Specific characteristics and dimensions of the layers can be modified as necessary to achieve desired results (e.g., high sample volume cryopreservation of cells). For example, the thickness of the layers can vary such that each of the bottom layer, the intermediate layer, and the top layer has a thickness between 100 to 500 μm. In some examples, the thickness of each of the bottom layer and the top layer is between 160 to 200 μm, e.g., 178 μm. In some examples, the thickness of the intermediate layer is between 100 to 140 μm, e.g., 120 μm.

In some examples, at least one of the bottom, the intermediate, and the top layers are made of a thermally conductive material. In such instances, the material has a thermal conductivity of at least 0.2 W m$^{-1}$ K$^{-1}$, at least 5 W m$^{-1}$ K$^{-1}$, at least 8 W m$^{-1}$ K$^{-1}$, or greater. In some examples, the bottom layer and the top layer have the same thermal conductivity. In some examples, the bottom, the intermediate, and the top layers have the same thermal conductivity.

In some examples, the thermally conductive material is a polymeric material. Non-limiting examples of a polymeric material for use in the vitrification cassettes described herein include polycarbonate, polymethyl methacrylate, polypropylene, styrene acrylonitrile, polyvinyl chloride, polyvinylidene chloride, polyethylene tetraphthalate, or combinations thereof. In some examples, the bottom and the top layers are made from a polymeric material and the intermediate layer comprises an adhesive material (e.g., a double sided pressure sensitive adhesive). In some examples, the bottom and the top layers are the same material. In some examples, the bottom, the intermediate, and the top layers are the same material.

Specific characteristics (e.g., shape, volume) and dimensions (e.g., outer dimensions) of the chamber can be modified as necessary to achieve desired results (e.g., high sample volume cryopreservation of cells). For example, the chamber can form various shapes such as a serpentine shape (see, e.g., FIG. 1A) or a cylinder shape (see, e.g., FIG. 1B).

In some examples, the chamber has a volume of 50 μL to 10 mL, e.g., 0.5 to 10 mL, 0.5 to 9 mL, 0.5 to 8 mL, 0.5 to 7 mL, 0.5 to 6 mL, 0.5 to 5 mL, 0.5 to 4 mL, 0.5 to 3 mL, 0.5 to 2 mL, 0.5 to 1 mL, 1 to 10 mL, 2 to 10 mL, 3 to 10 mL, 4 to 10 mL, 5 to 10 mL, 6 to 10 mL, 7 to 10 mL, 8 to 10 mL, or 9 to 10 mL.

In some examples, the chamber has a volume of 50 to 500 μL, e.g., 50 to 450 μL, 50 to 400 μL, 50 to 350 μL, 50 to 300 μL, 50 to 250 μL, 50 to 200 μL, 50 to 150 μL, 50 to 100 μL, 100 to 500 μL, 150 to 500 μL, 200 to 500 μL, 250 to 500 μL, 300 to 500 μL, 350 to 500 μL, 400 to 500 μL, or 450 to 500 μL.

In some examples, the chamber has outer dimensions of 40 to 450 mm by 15 to 250 mm, e.g., 45 to 65 mm by 15 to 45 mm (e.g., 52 mm by 40 mm) or 55 to 65 mm by 15 to 25 mm (e.g., 61 mm by 19 mm).

In some examples, the chamber has a height of between 50 to 150 μm, e.g., between 75 to 150 μm, between 100 to 150 μm, between 125 to 150 μm, between 50 to 125 μm, between 50 to 100 μm, or between 50 to 75 μm. In some examples, the chamber can have a height of 120 μm.

In some examples, the chamber has a surface area of 1,000 to 110,000 mm$^2$, 1,000 to 100,000 mm$^2$, 1,000 to 90,000 mm$^2$, 1,000 to 80,000 mm$^2$, 1,000 to 70,000 mm$^2$, 1,000 to 60,000 mm$^2$, 1,000 to 50,000 mm$^2$, 1,000 to 40,000 mm$^2$, 1,000 to 30,000 mm$^2$, 1,000 to 20,000 mm$^2$, 1,000 to 10,000 mm$^2$, 10,000 to 110,000 mm$^2$, 20,000 to 110,000 mm$^2$, 30,000 to 110,000 mm$^2$, 40,000 to 110,000 mm$^2$, 50,000 to 110,000 mm$^2$, 60,000 to 110,000 mm$^2$, 70,000 to 110,000 mm$^2$, 80,000 to 110,000 mm$^2$, 90,000 to 110,000 mm$^2$, or 100,000 to 110,000 mm$^2$.

In some examples, the chamber has a surface area of 2,500 to 10,000 mm$^2$, e.g., 5,000 to 10,000 mm$^2$, 7,500 to 10,000 mm$^2$, 2,500 to 7,500 mm$^2$, or 2,500 to 5,000 mm$^2$.

In some examples, the chamber has a ratio of surface area to volume of 0.1 to 25 mm$^{-1}$, e.g., 0.5 to 25 mm$^{-1}$, 1 to 25 mm$^{-1}$, 5 to 25 mm$^{-1}$, 10 to 25 mm$^{-1}$, 15 to 25 mm$^{-1}$, 20 to 25 mm$^{-1}$, 0.5 to 20 mm$^{-1}$, 0.5 to 15 mm$^{-1}$, 0.5 to 10 mm$^{-1}$, 0.5 to 5 mm$^{-1}$, or 0.5 to 1 mm$^{-1}$.

In some examples, the chamber has a ratio of surface area to volume of 0.1 to 1 mm$^{-1}$, e.g., 0.25 to 1 mm$^{-1}$, 0.5 to 1 mm$^{-1}$, 0.75 to 1 mm$^{-1}$, 0.1 to 0.75 mm$^{-1}$, 0.1 to 0.5 mm$^{-1}$, or 0.1 to 0.25 mm$^{-1}$.

The vitrification cassettes described herein include at least one port that is fluidly connected to the chamber, thereby allowing the cells in the vitrification solution to be loaded and unloaded from the chamber of the vitrification cassette. In such instances, the port is disposed in at least one of the layers (e.g., the port is disposed in the top layer and fluidly connected to the chamber).

In some examples, the port is sealed prior to submerging the vitrification cassette into liquid nitrogen. Any seal suitable for preventing contaminants from entering the chamber and/or preventing cells from exiting the chamber can be used in the vitrification cassettes described herein. In some examples, the seal is a polymeric seal or an adhesive seal. In such instances, the seal is penetrable by a needle for loading and unloading cells from the chamber. The seal can be in the form of a plug, a sheet (e.g., an adhesive sheet), a gasket, or a combination thereof.

In some examples, the port has a diameter between 1 to 5 mm, e.g., between 2 to 5 mm, between 3 to 5 mm, between 4 to 5 mm, between 1 to 4 mm, between 1 to 3 mm, or between 1 to 2 mm.

In some examples, the vitrification cassettes described herein include multiple ports, e.g., two ports, three ports, four ports, or more. In such instances, each port is fluidly connected to the chamber and is generally the same shape and diameter.

Any of the vitrification cassettes described herein can include at least one channel that is fluidly connected to the chamber. For example, when the port is sealed after loading, the cells cryopreserved and stored in the vitrification cassette can exit the chamber via the channel. In such instances, the cells can be expelled from the vitrification cassette using force created by centrifuging the vitrification cassette.

The vitrification cassettes described herein can vary in size and thickness. For example, the vitrification cassette has a size of 25 to 100 mm by 10 to 80 mm, e.g., 52 mm by 40 mm or 72 mm by 25 mm. For example, the vitrification cassette has a thickness between 0.4 to 1 mm, e.g., between 0.5 to 1 mm, between 0.6 to 1 mm, between 0.7 to 1 mm, between 0.8 to 1 mm, between 0.9 to 1 mm, between 0.4 to 0.9 mm, between 0.4 to 0.8 mm, between 0.4 to 0.7 mm, between 0.4 to 0.6 mm, or between 0.4 to 0.5 mm.

The vitrification cassettes described herein can be transparent to allow visual inspection of the chamber, which may assist loading and unloading of the vitrification cassette. In such instances, at least one of the bottom, the intermediate, and the top layers are made of a transparent material.

The vitrification cassette described herein, in some embodiments, is a composite of three layers of polycarbonate, held together in a sandwich by an appropriate adhesive such as an epoxy or pressure sensitive adhesive. The materials of the three layers are selected to have matching thermal expansion coefficients. These layers are each about 200 µm, but may be thicker or thinner to provide additional mechanical stability or reduced thermal mass. The middle layer is cut out to form the walls of a chamber, which is meant to contain the sample. The material is transparent to allow visual inspection of the chamber. The sample is loaded and unloaded by way of two ports, which are cut into the top sheet. Flexible gaskets are used to seal against the sheets, and to facilitate loading and unloading of the sample via these ports. The sample is retained within the gasket by capillary forces, but adhesive sheets can also be used to seal the ports. Prior to use, the ports are sealed by a disposable adhesive layer to protect the chamber from contamination. The chamber is laid out within the sandwich in a pattern that aids in loading and unloading of the sample. The planar geometry allows rapid heat exchange by high surface area to volume ratio, while also allowing large internal volumes relative to a capillary geometry. Heat is almost entirely exchanged along the normal axis, so the length and height of the device may be increased to accommodate larger sample volumes without greatly impacting heat exchange rate. The planar components are easy to manufacture and assemble, so the device can be produced in large volumes by reel-to-reel manufacturing processes.

EXAMPLES

In order that the invention described may be more fully understood, the following examples are set forth. The examples described in this application are offered to illustrate the methods and compositions provided herein and are not to be construed in any way as limiting their scope.

Materials and Methods

The following materials and methods were used in the Examples set forth herein.

Oocyst Sources and Collection Method

Fresh *C. parvum* oocysts (MD isolate of *cervine* origin passaged repeatedly in sheep and mice (Okhuysen et al., Infectivity of a *Cryptosporidium parvum* isolate of *cervine* origin for healthy adults and interferon-gamma knockout mice. *J Infect. Dis.* 185, 1320-1325 (2002))) were generated at the Tufts University by infection of four 8-week-old female CD-1 mice (Charles River Laboratories, Wilmington, MA). Propagation of oocysts in mice was conducted in an institution accredited by the Association for Assessment and Accreditation of Laboratory Animal Care (AAALAC) in compliance with the study protocol No. G2017-107 approved by the Tufts University Institutional Animal Care and Use Committee (IACUC) in accordance with the *Guide for the Care and Use of Laboratory Animals* (National Research Council).

Mice were grouped in bedded microisolators with access to food and water ad libitum. Mice were immunosuppressed throughout the course of experiment by administration of dexamethasone in drinking water at a concentration 16 mg/L. After three days of immunosuppressive treatment, each mouse received 50,000 oocysts in a PBS suspension by oral gavage. Starting from 5 DPI, which marks onset of fecal oocyst shedding, mice were kept in collection microisolators during the night for collection of fecal material and then rested in bedded microisolators during the day, both with access to food and water ad libitum. At termination of the experiment on 15 DPI, mice were euthanized by carbon dioxide asphyxiation, followed by cervical dislocation as required by the Tufts University IACUC guidelines. Oocysts were purified from mice feces by ether extraction and separated on a nycodenz gradient, as described elsewhere (Widmer, et al. Genotypic and phenotypic characterization of *Cryptosporidium parvum* isolates from people with AIDS. *J. Infect. Dis.* 178, 834-840 (1998)) with minor modifications. Briefly, homogenized fecal slurry was filtered through a 100 µm cell strainer and treated with diethyl ether in water containing 0.5% Tween 80 at the ratio 2:3. Oocysts were isolated by ultracentrifugation (13,400×g, 60 min) on a 10%/25% nycodenz gradient. Harvested oocysts were then resuspended in PBS and stored in 4° C. For consecutive propagation of fresh oocysts, intestines collected post-mortem from the positive control IFN-γ knockout mice (Jackson Laboratory, Bar Harbor, ME, USA) infected with unfrozen oocysts were utilized. Briefly, at the completion of the experiment, a section of gut was excised between duodenal bulb and rectum. Guts were homogenized with Tissue Master 125 homogenizer (Omni International, Kennesaw, GA, USA). Homogenized gut slurry was then processed as described above for fecal slurry with the exception of the filtration step using a cell strainer.

Oocyst Bleaching

Oocysts were bleached by incubation with either 5% or 20% dilutions of commercial bleach containing 8.25% sodium hypochlorite (CLOROX® Original, The Clorox Company, CA, USA). Following incubation with the indicated concentration of bleach on ice for 1 min, oocysts were then washed three times in PBS followed by centrifugation (18,000×g, 2 min) after each wash to remove supernatant.

Cell Lines

Madin-Darby Bovine Kidney (MDBK) cells (ATCC CCL-22) were maintained in the $CO_2$ incubator at 37° C. in RPMI media (Gibco) containing 10% heat-inactivated (56° C., 30 min) fetal bovine serum (FBS), 2 mM L-glutamine (Cellgro) and 100 U/penicillin/50 µg/mL streptomycin sulfate solution (MP Biomedicals). Cells were passaged weekly by serial subculture. Briefly, the cell monolayer was detached by incubation with 0.05% trypsin and 0.02% EDTA solution (Invitrogen) at 37° C. in the $CO_2$ incubator for 7 min. Collected cells were washed with fresh media, of which 10% was subcultured into the new flask.

CPA Pre-Freeze Toxicity In Vitro

Viability Testing

To increase the intracellular concentration of CPA, oocysts were bleached with various concentrations of bleach-5% or 20% and then incubated with CPA cocktails consisting of trehalose (Sigma) and DMSO (Sigma) at different concentrations. Briefly, bleached oocysts were first dehydrated in 1.6 M or 1 M trehalose solution for 10 min and then incubated for another 5-15 min with DMSO achieving its final concentration of 30% or 50% (ambient conditions were used throughout). The DMSO/trehalose cocktail was then diluted by incubation with excess PBS (at ratio 1:100) for 30 min at room temperature and removed by centrifugation (18,000×g, 2 min). Cytotoxicity attributable to the CPA cocktail was measured by inclusion of PI (Sigma) at 10

µg/mL using flow cytometry (ACCURI® C6, BD Life Sciences) and was normalized to its control in PBS for each condition.

In an effort to maximize the concentration of intracellular and extracellular CPA without compromising oocyst viability, oocysts were gradually exposed to higher concentrations of DMSO by two-step addition. Here, 6-week-old bleached oocysts (5% or 20%) were first dehydrated in 1.6 M trehalose for 10 min. DMSO was added to achieve 0.8 M trehalose/30% DMSO solution and incubated for 5 min. The second addition of DMSO led to a final concentration of 0.5 M trehalose/50% DMSO and was incubated for 1 min. CPA cocktail was then diluted as described above. Cytotoxicity attributable to CPA cocktail was measured by inclusion of PI and was normalized to the untreated oocyst control in PBS.

Infectivity Testing In Vitro

Figure 2A:
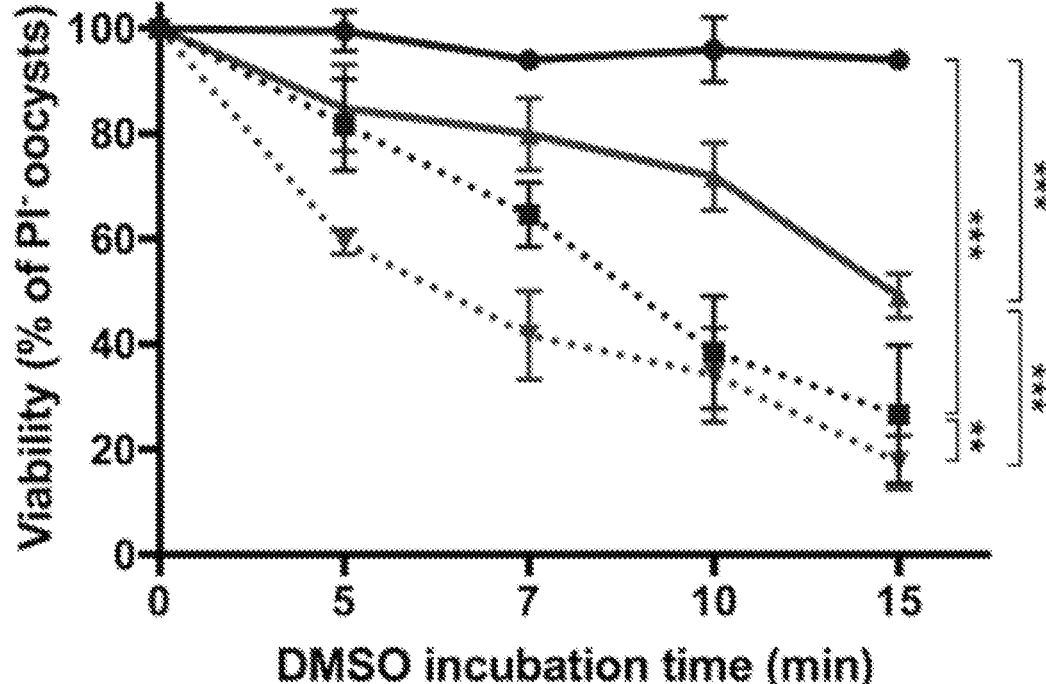
FIG. 2A is a graph showing viability of oocysts permeabilized with either 5% or 20% bleach, followed by incubation with a CPA cocktail containing varying concentrations of trehalose and DMSO over a duration of 5-15 min. Viability was measured by PI exclusion after removal of CPA (n=3). Differences in viability in response to bleaching and trehalose/DMSO treatment were measured using two-way ANOVA (*p<0.0001; p=0.002).
Figure 2B:
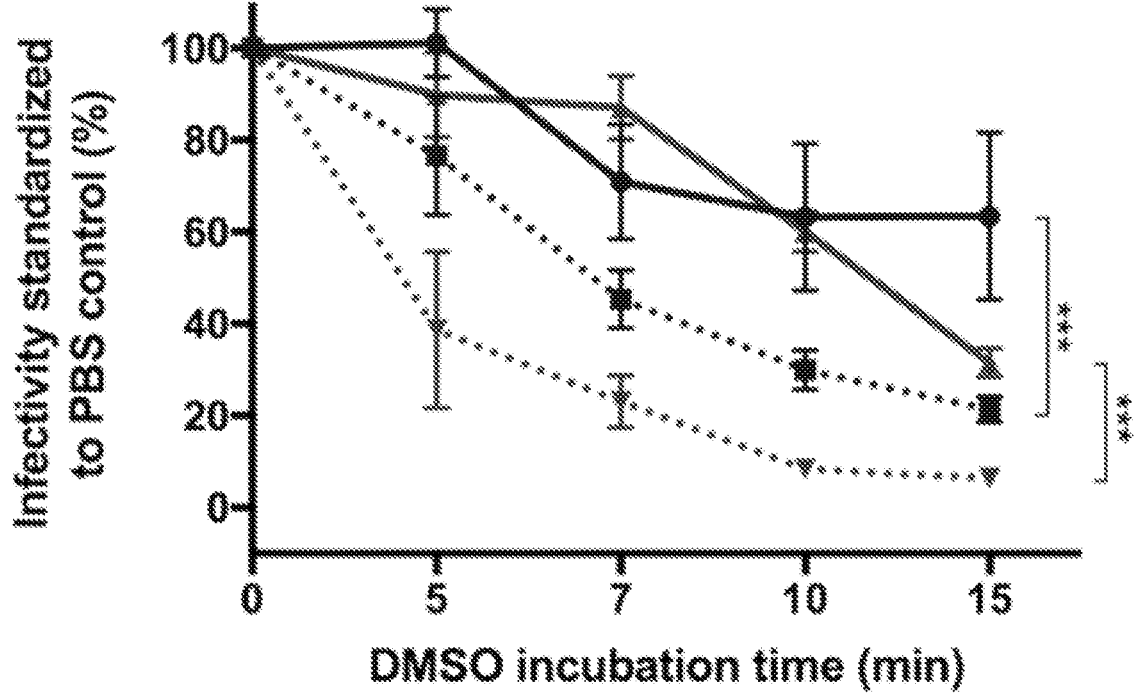
FIG. 2B is a graph showing infectivity of oocysts permeabilized with either 5% or 20% bleach, followed by incubation with a CPA cocktail containing varying concentrations of trehalose and DMSO over a duration of 5-15 min. Infectivity was measured as percent of intracellular parasitic stages established in MDBK cells in comparison to control oocysts incubated with PBS in lieu of DMSO (n=4). Differences in infectivity in response to DMSO concentration were measured for both permeabilization/dehydration protocols using two-way ANOVA (***p<0.0001).

All CPA cocktails described in FIG. 2A were further tested for infectivity in the in vitro model of epithelial cell infection using MDBK cells. Twenty thousand cells were seeded into each well of a 96-well culturing plate (Falcon) and maintained for two days to reach confluence (defined at $4×10^4$/well). Oocysts were prepared for infection by bleaching and incubation with CPA cocktail as described above. After removal of diluted CPA in excess PBS, the oocyst pellet was resuspended in 50 µL of 0.75% sodium tauro-cholate (Sigma) and incubated at 37° C. for 15 min to prompt excystation. Pre-excysted oocysts were then added onto confluent cell monolayers at MOI 1:3. After 24-h co-incubation of parasite with cell monolayer, cultures were washed with PBS to remove extracellular stages of parasite, permeabilized with 100% methanol for 10 min at room temperature and then washed again with PBS. After fixation, cells were blocked with 10% FBS for 30 min and then incubated with fluorescein-labeled *Vicia villosa* lectin (Vector Laboratories) at concentration 1 g/mL for 30 min to visualize intracellular stages of the parasite. After the final wash with PBS, monolayers were inspected with a Nikon ECLIPSE® Ti-E microscope (Nikon Instruments Inc.). Four images were taken of each well at 200× magnification using a FITC filter at 100 ms exposure. The number of fluorescing infection foci was then counted by ImageJ 1.48v particle analyzer using the following settings: triangle threshold 15-255, size exclusion at 10-1,000 pixel$^2$ and circularity at 0.1-1.0. Results depicted in FIG. 2B are expressed as percent infectivity of the control oocysts, which were treated with PBS in place of CPA.

Vitrification Cassettes

The vitrification cassette consists of two sheets of polycarbonate laminates (thickness 178 µm) bonded by a sheet of pressure sensitive adhesive (thickness 120 µm) which is cut out to form a chamber. The top sheet of polycarbonate has two holes on either end of the chamber for sample loading and unloading. Sample is loaded using two 0.2-1 mL pipette tips fixed with punched PDMS gaskets with 4 mm outer and 1 mm inner diameter (Drummond Scientific). The chamber is shaped in a serpentine to avoid trapping bubbles during sample loading, and to improve sample recovery by flushing. The chamber outer dimensions are 52 mm by 40 mm and internal volume approximately 200 µL (FIG. 7A). The cassettes can be produced in large volumes by existing reel-to-reel manufacturing processes. Fabrication services were provided by Grace BioLabs (Bend, OR, USA) using an AutoCAD file as a template.

Rapid cooling in the cassettes was validated by imaging at 20× magnification. Water-DMSO mixtures were rapidly plunged in liquid nitrogen, then removed and imaged under a stereomicroscope Zeiss Stemi 508 (Carl Zeiss Microscopy, Germany) while gradually rewarming. Ice crystallization during gradual warming in air (transition from transparent to opaque white) is observed >25% v/v DMSO, indicating successful vitrification.

Cryopreservation Protocols for Ultra-Rapid Cooling of Oocysts

Cryopreservation Using Larger Commercially Available Specimen Containers

The vitrification protocol previously reported using microcapillaries (Jaskiewicz et al., Cryopreservation of infectious *Cryptosporidium parvum* oocysts. *Nat. Commun.* 9, 2883 (2018)) was applied with modifications to larger containers such as a polyethylene terephthalate insemination straw (CryoBio System, France) and an ultra-clear USP class IV polycarbonate cryovial (VWR). The concentration of DMSO was increased from 30 to 40% to account for decreased rate of temperature transfer as a result of an increase in container diameter and wall thickness. Additionally, polyvinylpyrrolidone (PVP) (Sigma) was added to DMSO in order to ensure glass formation and prevent ice crystallization upon thawing. Briefly, bleached oocysts (5%, 1 min) were incubated in 1 M trehalose for 10 min. A cocktail of DMSO and PVP was then added to achieve a final concentration of 0.5 M trehalose/6% PVP/40% DMSO and incubated for 5 min at room temperature. Fifty µL aliquots were then frozen in an insemination straw or a cryovial by rapidly plunging in liquid nitrogen and then thawed in a 40° C. water bath for 30 s. Expelled contents were incubated in excess PBS and processed as described above.

Cryopreservation Using Novel High Aspect Ratio Specimen Containers

Briefly, 2,000,000 *C. parvum* MD oocysts were treated with 20% CLOROX® bleach for 1 min on ice and then washed with PBS. Oocysts were centrifuged (18,000×g, 2 min), resuspended in 20 µL of 1.6 M trehalose and incubated at room temperature for 10 min. Next, 20 µL of 60% DMSO was added to dehydrated oocysts to achieve the concentration of 0.8 M trehalose/30% DMSO and was incubated for 5 min at room temperature. Lastly, 20 µL of 90% DMSO was added to achieve final concentration of 0.5 M trehalose/50% DMSO. Following the second addition of DMSO, oocysts were loaded into polycarbonate cassettes (Grace Biolabs #RD500011; 52 mm×40 mm) in the following manner: 60 µL of oocysts in CPA cocktail was loaded onto the cassette port and was aspirated into the cassette via negative pressure created by removing the air from the opposite port with 1 mL pipette tip fixed with punched PDMS gasket (Drummond Scientific). While the study described herein utilized 60 µL inocula containing 2,000,000 oocysts at a time, a single cassette can hold more than three times this volume. Loaded cassettes were then rapidly submerged in liquid nitrogen such that exposure to 50% DMSO did not exceed 1 min. Although the sample reaches cryogenic temperatures nearly instantaneously, oocysts were maintained in liquid nitrogen for 10 min prior to thawing. Thawing was achieved by quickly transferring the cassette from liquid nitrogen to a 40° C. water bath for 20 s. It is critical that the cassette be rapidly transferred into liquid nitrogen, as well as be rapidly transferred from liquid nitrogen to 40° C. for thawing, in order to avoid lethal ice crystallization. Contents of the cassette were expelled using hydraulic pressure applied by flushing PBS through the cassette port sealed with PDMS gasket attached to the 1 mL pipette tip. The contents expelled through the opposite port were collected with pipette and transferred to 1.5 mL tube to incubate in excess PBS for 30 min at room temperature. Supernatant was then removed from samples by centrifugation (18,000×g, 2 min) and 100 µL of PBS was used to resuspend the pellet. Thawed oocysts were stored on ice prior to further testing.

Modification of the protocol described above with a one-step DMSO addition, was also tested using rectangular capillaries and vitrification cassettes. Here, oocysts were incubated in 1.6 M trehalose for 10 min and then in DMSO for 5 min achieving final concentration of 0.8 M trehalose/ 50% DMSO, before being frozen in liquid nitrogen for 10 min using either rectangular borosilicate glass capillaries (VitroTubes 0.2×2 mm, Vitrocom) or polycarbonate cassettes, as described above. Samples were then thawed in 40° C. water bath for 20 s. Expelled contents were incubated in excess PBS and processed as described above.

In Vitro Viability and Infectivity of Cryopreserved Oocysts

Bleached (20%) C. parvum oocysts at 1-2, 6 and 12 weeks of age were cryopreserved as described above using a two-step DMSO addition protocol, such that final concentration of 0.5 M trehalose/50% DMSO was achieved. Oocysts exposed to cryoprotective cocktails but not frozen were also studied to discern lethality due to CPA toxicity rather than freezing. Pre-freeze and post-freeze oocyst viability was measured by PI exclusion at 10 µg/mL using flow cytometry and by an in vitro infectivity assay. Briefly, MDBK cells were prepared for infection as described above. Cells were infected with cryopreserved oocysts at MOI 1:1. After 24 h incubation with parasites, cells were processed following the immunofluorescence protocol as described above in order to detect intracellular stages of the parasite. Micrographs of infection were taken under 200× magnification using FITC filter at 100 ms exposure (Nikon Instruments Inc.).

For evaluation of cryopreservation in insemination straws and cryovials, pre-freeze and post-freeze viability was measured only by PI exclusion as described above.

In Vivo Infectivity of Cryopreserved Oocysts

C. parvum oocysts at 2, 6 and 12 weeks of age were bleached (20%) and cryopreserved in the vitrification cassettes as described above using a two-step DMSO addition protocol with final concentration of 0.5 M trehalose/50% DMSO. Infectivity of cryopreserved oocysts was evaluated in 8-week-old female IFN-γ knockout mice bred under pathogen-free conditions (Jackson Laboratory, Bar Harbor, ME, USA). All mice experiments were conducted in an AAALAC accredited institution in compliance with the study protocol No. G2017-107 approved by the Tufts University Institutional Animal Care and Use Committee in accordance with the *Guide for the Care and Use of Laboratory Animals* (National Research Council). Mice were randomly assigned into groups of three by a blinded animal caretaker, however the investigators were not blinded during this experiment.

The animal care, inoculation and monitoring procedures were performed as described elsewhere (Jaskiewicz et al., Cryopreservation of infectious *Cryptosporidium parvum* oocysts. *Nat. Commun.* 9, 2883 (2018)), with modifications. Mice were immunosuppressed throughout the course of the experiment by administration of dexamethasone in drinking water at concentration 10 mg/L. Three days after immunosuppressive treatment started, each mouse received 30,000 PI⁻ cryopreserved oocysts in PBS suspension by oral gavage. Each batch of experiments was performed in the presence of a positive control group (mice inoculated with 30,000 fresh PI⁻ oocysts) and a negative control group (mice inoculated with 30,000 heat-inactivated oocysts). For evaluation of fecal oocyst shedding, feces were collected daily from each mouse individually starting from 3 DPI. Mice demonstrating evidence of fecal oocyst shedding were euthanized by carbon dioxide asphyxiation followed by cervical translocation on 7 DPI, unless prematurely terminated due to recumbency. Mice negative for signs of infection were monitored until 11 DPI. Intensity of fecal shedding was measured daily by inspection of the acid-fast stained fecal smear slides, prepared from a single fecal pellet of approximately equal size, for presence of oocysts in 30 fields (1000×).

The animal experiments which produced negative cryopreservation outcome were performed as described above with exception of few procedural details. A summary table describing the different cryopreservation methods evaluated and the corresponding outcome can be found in Table 1. Briefly, for evaluation of one-step DMSO cryopreservation protocol in vitrification cassettes and rectangular capillaries, 6- and 2-week-old oocysts were used, respectively, and animals were infected with a dose of 10,000 PI⁻ oocysts. For evaluation of cryopreservation outcome in insemination straws and cryovials, 8-week-old oocysts were used and mice received a dose of 5,000 PI⁻ oocysts. Although mice were inoculated with a higher number of oocysts using the protocol described for vitrification cassettes, positive infection was most likely due to use of the improved cryopreservation protocol provided herein as evidenced by the observation that the course of infection between thawed and untreated oocysts were similar.

Statistical Analysis

All in vitro infection experiments were performed in two technical repeats and were replicated three or four times to ensure reproducibility. All in vitro viability experiments were performed in triplicate. For in vivo experiments groups of 3 animals were used to assess oocyst infectivity. Graphing and statistical analyses of data were performed using Graph-Pad Prism software (v7.0c, GraphPad Software, Inc.).

Example 1: Oocysts Cryopreserved in Commercially Available Containers are not Viable or Infectious To enable cryopreservation of increased sample volumes, a range of commercially available specimen containers that allow ≥200 µL were initially tested including cryovials and insemination straws for compatibility with the CPA loading protocol (Jaskiewicz et al., Cryopreservation of infectious *Cryptosporidium parvum* oocysts. *Nat. Commun.* 9, 2883 (2018)), with modifications (FIG. 5A). Specifically, as the thermal mass of the sample is increased in these larger specimen containers, the CPA concentration must also be increased to facilitate vitrification. This was accomplished by increasing the concentration of DMSO from 30 to 40%. The CPA solution was further supplemented with polyvinylpyrrolidone (PVP), an extracellular CPA that reduces ice crystallization during thawing. When this CPA solution of DMSO and PVP was loaded into the specimen containers and submerged in liquid nitrogen, visual examination indicated a vitreous state was achieved. Although oocyst viability assessed by propidium iodide (PI) exclusion ranged between 25-35% (35.5±3.4% for cryovial and 25.3±7.1% for insemination straw) after thawing, oocysts failed to infect IFN-γ knockout mice (FIGS. 5A-5B). This failure is likely due to damage induced by the formation of lethal intracellular ice crystals as a consequence of insufficient CPA concentration within the oocyst. Accordingly, as the cooling rate is reduced to ~$10^3$° C./min, a higher concentration of CPA is required to prevent ice crystal formation inside of the oocysts. Taken together, these results demonstrate that commercially available containers including cry-ovials and insemination straws failed to cryopreserve viable and infectious *C. parvum* oocysts.

Example 2: Development of High Aspect Ratio Specimen Containers to Enable Vitrification of Bulk Volumes High aspect ratio specimen containers were developed that maintain high cooling rates while simultaneously increasing sample volume. Initially, a commercially available borosilicate glass rectangular capillary that holds a volume of up to 40 μL was used, but it was very fragile and shattered easily (FIG. 6A). Next, a polycarbonate vitrifica-tion cassette based on a high aspect ratio model was designed (FIGS. 1A-1B, FIG. 6B, FIGS. 7A-7B). This cassette increases the sample volume to approximately 200 μL with minimal reduction of the cooling rate, estimated at $10^{4°}$ C./min when plunged into liquid nitrogen, based on extrapolation from the observation of partial vitrification of a 25% v/v DMSO/water solution (He et al., Vitrification by ultra-fast cooling at a low concentration of cryoprotectants in a quartz micro-capillary: a study using murine embryonic stem cells. *Cryobiology* 56, 223-232 (2008); Hopkins et al., Effect of common cryoprotectants on critical warming rates and ice formation in aqueous solutions. *Cryobiology* 65, 169-178 (2012)). Given that a minimum of 30% DMSO was necessary to form extracellular glass in the vitrification cassettes, 50% DMSO was selected to maximize glass formation within the oocyst since the intracellular concen-tration of CPA is likely much lower than that present in the extracellular solution (FIG. 5C).

Example 3: Hypochlorite Treatment Improves CPA Uptake

Given the impermeable nature of the oocyst wall, an approach to increase CPA uptake is through improved per-meabilization. Previously, treatment with hypochlorite was found to enable partial uptake of CPAs (Jaskiewicz et al., Cryopreservation of infectious *Cryptosporidium parvum* oocysts. *Nat. Commun.* 9, 2883 (2018)). Trehalose was then added to induce osmotic dehydration of oocysts, thereby increasing the overall concentration of CPAs within the oocyst and reducing the risk of formation of intracellular ice crystals. Here, this effect was enhanced by applying harsher bleaching conditions and increasing the osmotic trehalose gradient. Oocysts permeabilized by bleach and dehydrated in trehalose, both in increasing concentrations, were subse-quently exposed to varying concentrations of DMSO (30% and 50%) over a 15 min period and evaluated for viability as an indirect measure of CPA uptake. FIG. 2A-2B illustrate the fitness of oocysts based on their viability and infectivity in vitro following CPA removal and recovery in PBS. Harsher bleaching conditions were found to increase per-meability of oocysts to DMSO, both at 30% and 50% concentration, as evidenced indirectly by an observed increase in mortality rates. Oocysts incubated with 50% DMSO maintained acceptable viability and in vitro infec-tivity during 5 min of incubation (for 20% bleach condition: 59.4±2.3% viability, 38.7±17.0% in vitro infectivity). How-ever, after 15 min or longer, DMSO at this concentration was found to be highly toxic (for 20% bleach condition: 17.5±5.0% viability and 6.4±1.9% infectivity). Oocysts exposed to the cocktail of 0.8 M trehalose/50% DMSO for 5 min and then subsequently cooled using both types of high aspect ratio specimen containers (i.e., rectangular capillary or cassette), were not infectious to IFN-γ knockout mice (FIG. 6C).

These results demonstrate that 50% DMSO, although important for vitrification in these specimen containers, accumulates significant pre-freeze and post-thaw cytotoxic-ity, rendering oocysts non-infectious.

Figure 2C:
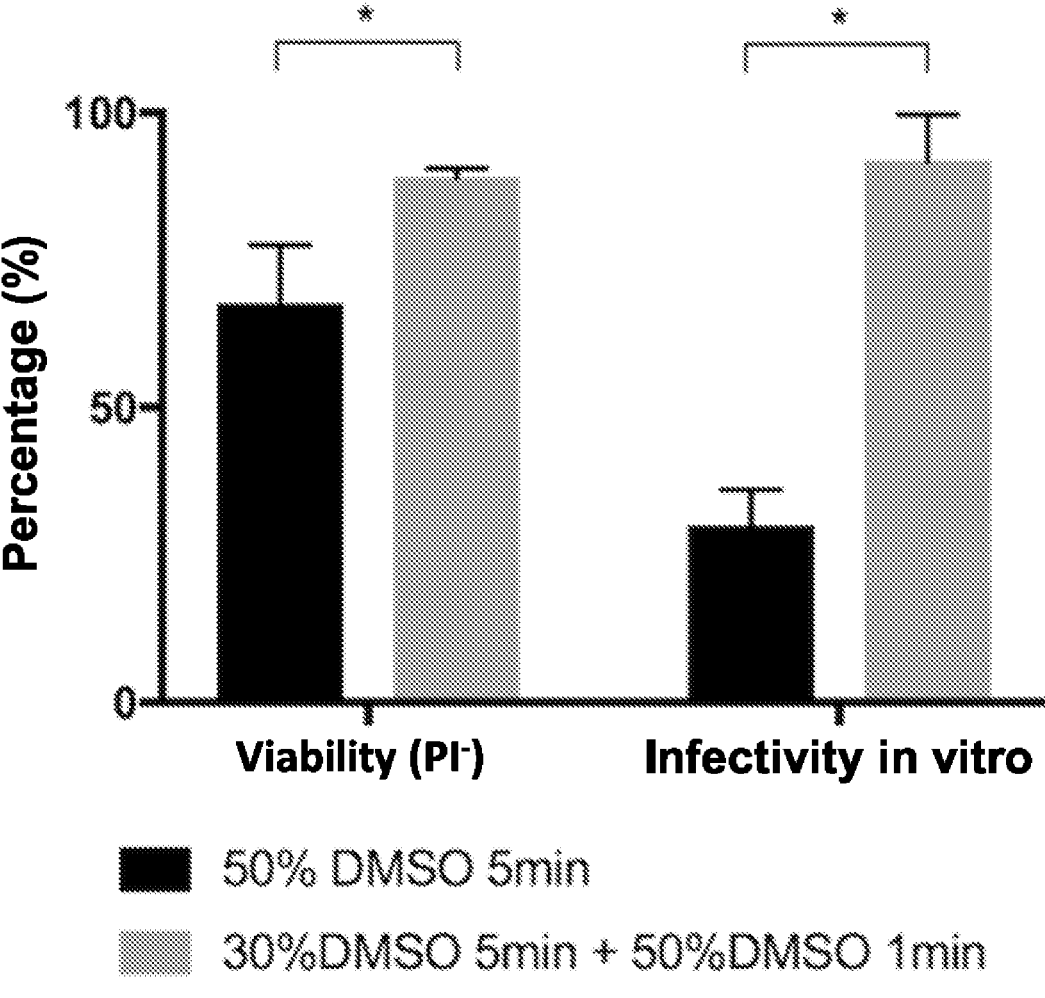
FIG. 2C is a graph showing toxicity due to CPA alone (pre-freeze) measured in terms of viability and in vitro infectivity following treatment with 50% DMSO in either one- or two-step additions. Viability is reported as percent of $PI^-$ oocysts and infectivity as percent of intracellular parasitic stages established in MDBK cells in comparison to control oocysts incubated with PBS in lieu of DMSO (n=3). Differences between treatments were measured using Mann-Whitney test (*p=0.05). All values indicate means and error bars indicate standard deviation.

Example 4: Two-Step CPA Loading Increased Pre-Freeze Viability and Infectivity To ensure glass formation in the vitrification cassettes, the intracellular concentration of DMSO was increased while minimizing cytotoxicity. This was accomplished by adding DMSO in a step-wise manner rather than all at once, such that a final extracellular concentration of 50% is achieved with reduced toxicity. In this approach, oocysts were first incubated in 30% DMSO for 5 min, and then 50% DMSO for one additional minute. This significantly increased pre-freeze viability and infectivity in vitro in comparison to the one-step DMSO addition at the same overall concentration (FIG. 2C). Based on low oocyst permeability, in the two-step protocol, the additional DMSO (50% v/v) is unlikely to accumulate substantially inside the oocyst as the duration of exposure is limited to 1 min. However, it was previously observed that oocysts substantially dehydrate in response to the hyperosmotic extracellular gradient created by extracel-lular DMSO (Jaskiewicz et al., Cryopreservation of infec-tious *Cryptosporidium parvum* oocysts. *Nat. Commun.* 9, 2883 (2018)). Thus, the initial low concentration of DMSO within the oocyst can increase as a result of water loss caused by the osmotic gradient applied during the second CPA loading step. Given this minimal toxicity, the two-step DMSO loading protocol was examined for the cryopreser-vation of oocysts using the vitrification cassettes.

Figure 3A:
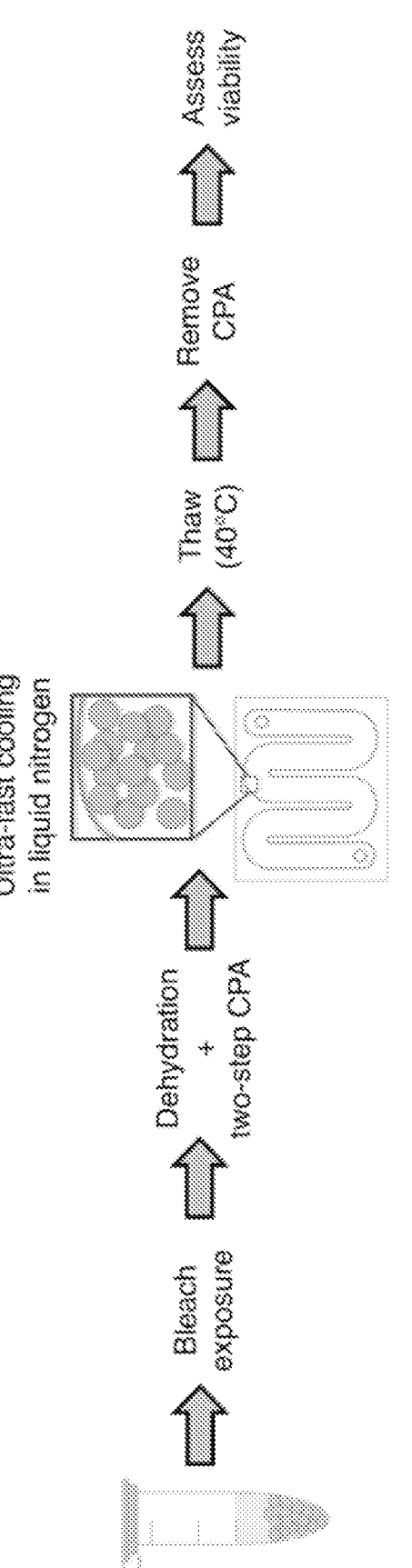
FIG. 3A is a schematic depiction of methods for cryopreservation by vitrification using vitrification cassettes, in accordance with some embodiments of the technology described herein.
Figure 3B:
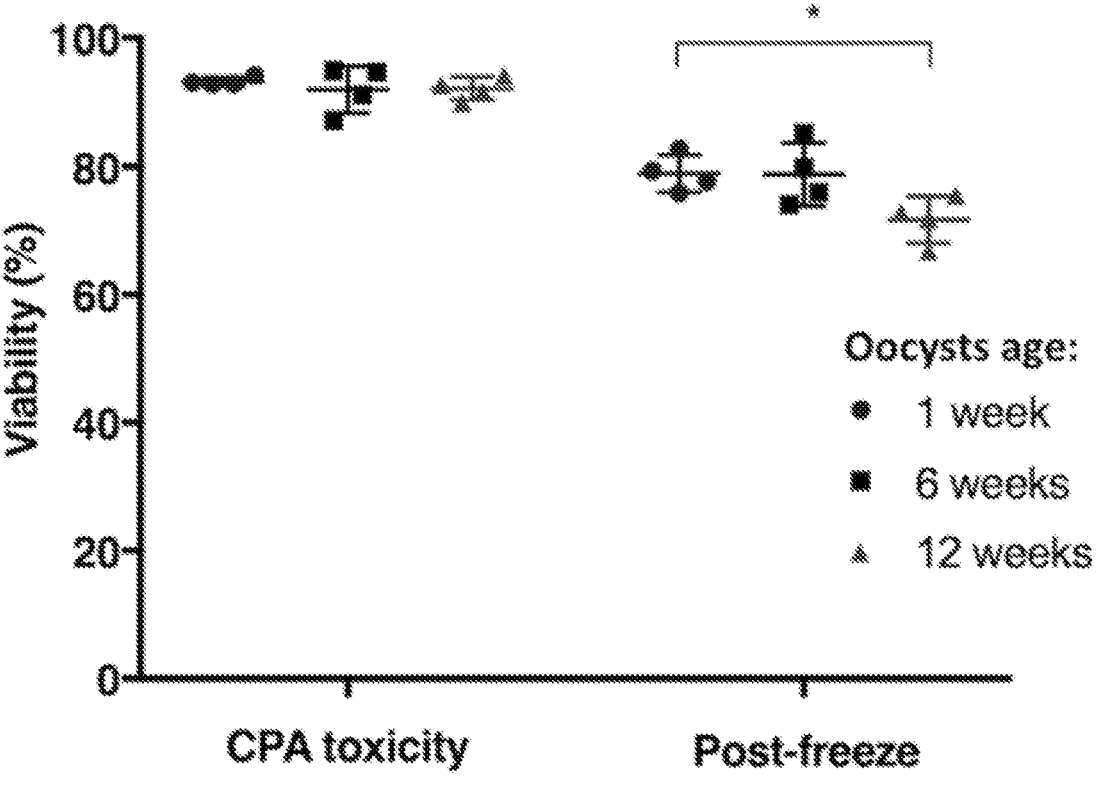

Example 5: Cryopreservation In Vitrification Cassettes Yields Oocysts that Exhibit In Vitro Infectivity Oocyst age is important for cryopreservation outcome (Jaskiewicz et al., Cryopreservation of infectious *Cryp-tosporidium parvum* oocysts. *Nat. Commun.* 9, 2883 (2018)), and therefore methods and cassettes described herein were tested on a single batch of oocysts at different ages: 1, 6 and 12 weeks. FIG. 3A shows the workflow used in these vitrification experiments. First, oocysts were per-meabilized by treatment with 20% bleach for 1 min and then suspended in 1.6 M trehalose for 10 min to promote dehy-dration. Next, a final concentration of 50% DMSO/0.5 M trehalose was achieved using the stepwise CPA loading protocol described above. The sample was then loaded into a vitrification cassette and rapidly submerged in liquid nitrogen for 10 min to ensure the specimen was fully vitrified. While 10 min under liquid nitrogen may be brief, this is sufficient time for the specimen to equilibrate at −196° C. At this temperature, enzymatic activity essentially stops, and therefore the quality of the specimen at 10 min is reflective of the quality expected under much longer storage durations. The sample was later thawed by brief submersion in a 40° C. water bath. FIG. 3B shows the toxicity associated with CPA exposure for oocysts of different ages, as com-pared to the post-thaw toxicity caused cumulatively by CPA exposure and cryopreservation. Cryopreservation yielded 70-80% viable oocysts based on PI exclusion. While CPA toxicity alone reduced viability to ~92% regardless of oocyst age, the oldest oocysts exhibited significantly increased mortality after thawing (78.9±2.5%, 78.8±4.2% and 71.7±3.1% at 1-, 6- and 12-weeks, respectively). As exclusion of PI alone is found to be an inaccurate marker of viability (VandeBurgt et al., Comparison of in vitro viability methods for *Cryptosporidium* oocysts. *Exp. Parasitol.* 187, 30-36 (2018); and Black et al., Comparison of assays for *Cryptosporidium parvum* oocysts viability after chemical disinfection. *FEMS Microbiol. Lett.* 135, 187-189 (1996)), oocyst viability testing was coupled with the in vitro infectivity assay. Cryopreserved oocysts were found to invade and establish intracellular stages inside MDBK cells, with the exception of 12-week-old oocysts (FIG. 3C), which failed to invade. These results are consistent with previous observations in which oocysts cryopreserved at an older age exhibit reduced infectivity in animals (Jaskiewicz et al., Cryopreservation of infectious *Cryptosporidium parvum* oocysts. *Nat. Commun.* 9, 2883 (2018)).

Example 6: Cryopreservation In Vitrification Cassettes Yields Oocysts that are Infectious In Vivo Based on the promising results obtained from in vitro testing, the infectivity of thawed oocysts was assessed using the IFN-γ knockout mouse model. FIGS. 4A-4C show that oocysts of different ages (2, 6 and 12 weeks) cryopreserved in liquid nitrogen for 10 min using the vitrification cassettes were infectious to mice. Specifically, mice inoculated with cryopreserved oocysts developed a patent infection at 4 days post infection (DPI), a day later than mice inoculated with unfrozen control oocysts, as evidenced by onset of fecal oocyst shedding. Contrary to our in vitro findings, no reduction in oocyst infectivity in vivo as a function of oocyst age was observed, as inferred from the onset of oocyst shedding on the same day. This data demonstrates that oocysts aged up to 12 weeks can be successfully cryopreserved using vitrification cassettes. It is estimated that $\sim 10^7$ oocysts can be obtained from one mouse infected with cryopreserved oocysts by direct purification from intestines collected post mortem. Additionally, collection of feces throughout the course of infection can further maximize the total output of oocysts. Oocysts cryopreserved in commercially available containers and oocysts cryopreserved in vitrification cassettes using one-step CPA loading were not infectious in animals after thawing.

A summary of the various methods used to cryopreserve oocysts and whether the cryopreserved oocysts were infectious after thawing is provided below in Table 1.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for high-volume cryopreservation of a plurality of cells by vitrification, the method comprising:

(a) incubating the cells in a vitrification solution comprising a dehydrating agent for a time and under conditions sufficient to dehydrate the cells;

(b) adding one or more cryoprotective agents (CPAs) to the vitrification solution at a total CPA concentration of up to 30% and incubating the cells in the vitrification solution for a time and under conditions sufficient for uptake of the one or more CPAs by the cells;

(c) after step (b), adding an additional amount of the one or more CPAs to the vitrification solution to increase a total concentration of the one or more CPAs in the vitrification solution by at least an additional 10% and incubating the cells for up to one minute;

(d) loading the cells in the vitrification solution into a vitrification cassette, wherein the vitrification cassette comprises:

a planar bottom layer;

a planar top layer;

a planar intermediate layer disposed between the bottom layer and the top layer and enclosing a chamber within the intermediate layer, wherein the chamber has a height of about 50 to about 150 μm, a volume of at least 200 μL to 500 μL, and outer dimensions of the planar top layer and planar bottom layer of about 25 to about 100 mm by about 15 to about 80 mm; and at least one port fluidly connected to the chamber, wherein the bottom, the intermediate, and the top layers are laminated together or held together mechanically; and (e) cooling the cells in the vitrification solution in the vitrification cassette to a temperature less than or equal to a glass transition temperature of the vitrification

TABLE 1

| Summary of cryopreservation methods and their outcome in animal models. | | | | | | | |
|---|---|---|---|---|---|---|---|
| Specimen Container | Age of oocysts | Concentration of trehalose (initial/final) | DMSO addition protocol | CPA concentration | DMSO incubation time | Inoculation dose | Infectivity in animals after thawing |
| Insemination straw | 8 weeks | 1M/0.5M | One-step | 40% DMSO (+6% PVP) | 5 min | 5,000 | No |
| Cryovial | 8 weeks | 1M/0.5M | One-step | 40% DMSO (+6% PVP) | 5 min | 5,000 | No |
| Rectangular capillary | 2 weeks | 1.6M/0.8M | One-step | 50% DMSO | 5 min | 10,000 | No |
| Vitrification cassette | 6 weeks | 1.6M/0.8M | One-step | 50% DMSO | 5 min | 10,000 | No |
| Vitrification cassette | 2-12 weeks | 1.6M/0.5M | Two-step | 30% DMSO/ 50% DMSO | 5 min/ 1 min | 30,000 | Yes |

25

26 solution at a rate equal to or greater than 30,000° C./minute, wherein the cooling causes vitrification of the plurality of cells.

2. The method of claim 1, wherein the dehydrating agent is a salt, a sugar, or a combination thereof.

3. The method of claim 2, wherein the dehydrating agent is a sugar comprising sucrose, trehalose, raffinose, stachyose, dextran, or a combination of any two or more thereof.

4. The method of claim 1, wherein the one or more cryoprotective agents are selected from the group consisting of glycerol, ethylene glycol, 1,2-propanediol, and dimethyl sulfoxide (DMSO).

5. The method of claim 1, wherein step (c) comprises increasing the total concentration of the one or more cryoprotective agents in the vitrification solution by at least 15%.

6. The method of claim 1, wherein the cells in the vitrification solution are cooled at a rate equal to or greater than 100,000 to 250,000° C./minute.

7. The method of claim 1, further comprising, prior to step (a), exposing the cells to a permeabilization solution comprising a permeabilizing agent for a time and under conditions sufficient to increase uptake of the cryoprotective agent by the cells compared to uptake of the cryoprotective agent by untreated cells.

8. The method of claim 7, wherein the permeabilizing agent is hypochlorite.

9. The method of claim 1, wherein a level of infectivity or viability, or both, of the cells after vitrification is at least 50% of the level of infectivity or viability, or both, of untreated cells.

10. The method of claim 1, wherein the cells are oocytes.

11. The method of claim 1, wherein the one or more CPAs comprise DMSO.

12. The method of claim 1, wherein the dehydrating agent comprises trehalose and the one or more CPAs comprise DMSO.

13. The method of claim 1, wherein in step (c) the concentration of the one or more CPAs in the vitrification solution is increased to a total concentration of up to 50%.

14. The method of claim 13, wherein the dehydrating agent is a salt, a sugar, or a combination thereof.

15. The method of claim 14, wherein the dehydrating agent is a sugar comprising sucrose, trehalose, raffinose, stachyose, dextran, or a combination of any one or more thereof.

16. The method of claim 13, wherein the one or more CPAs are selected from the group consisting of glycerol, ethylene glycol, 1,2-propanediol, and dimethyl sulfoxide (DMSO).

17. The method of claim 16, wherein the one or more CPAs comprise DMSO.

18. The method of claim 16, wherein the dehydrating agent comprises trehalose and the one or more CPAs comprise DMSO.

* * * * *